(12) United States Patent
Levin et al.

(10) Patent No.: US 11,740,177 B2
(45) Date of Patent: Aug. 29, 2023

(54) INTERFEROMETRIC DETECTION AND QUANTIFICATION SYSTEM AND METHODS OF USE IN AQUATICS

(71) Applicant: Salvus, LLC, Valdosta, GA (US)

(72) Inventors: Ron Levin, Valdosta, GA (US); Clinton Beeland, Valdosta, GA (US); James LeFiles, Valdosta, GA (US); Joseph Egan, Atlanta, GA (US); Timothy Zollers, Atlanta, GA (US); Jacob Thompson, Atlanta, GA (US)

(73) Assignee: SALVUS, LLC, Valdosta, GA (US)

( * ) Notice: Subject to any disclaimer, the term of this patent is extended or adjusted under 35 U.S.C. 154(b) by 0 days.

(21) Appl. No.: 17/448,079

(22) Filed: Sep. 20, 2021

(65) Prior Publication Data

US 2022/0091030 A1 Mar. 24, 2022

Related U.S. Application Data

(60) Provisional application No. 63/080,204, filed on Sep. 18, 2020.

(51) Int. Cl.
| | | |
|---|---|---|
| *G01J 3/45* | (2006.01) | |
| *G01N 21/45* | (2006.01) | |
| *G01N 33/53* | (2006.01) | |
| *G01N 21/77* | (2006.01) | |

(52) U.S. Cl.
CPC ............... *G01N 21/45* (2013.01); *G01J 3/45* (2013.01); *G01N 21/77* (2013.01); *G01N 33/5308* (2013.01); *G01N 2021/7779* (2013.01)

(58) Field of Classification Search
CPC .... G01N 21/45; G01N 21/77; G01N 33/5308; G01N 2021/7779; G01N 33/54373; G01N 21/0332; G01N 2021/158; G01N 2021/7763; G01N 2201/0221; G01N 21/77; G01J 3/45
See application file for complete search history.

(56) References Cited

U.S. PATENT DOCUMENTS

| | | | |
|---|---|---|---|
| 7,630,063 B2* | 12/2009 | Padmanabhan | A61B 5/157 |
| | | | 436/63 |
| 8,502,985 B2* | 8/2013 | Weinberger | G01N 21/0332 |
| | | | 356/450 |
| 2005/0135723 A1 | 6/2005 | Carr et al. | |
| 2012/0214707 A1* | 8/2012 | Ymeti | G01N 21/45 |
| | | | 506/15 |
| 2017/0189906 A1 | 7/2017 | Moll et al. | |
| 2022/0091031 A1* | 3/2022 | Levin | G01N 21/85 |
| 2022/0091086 A1* | 3/2022 | Levin | H04N 5/22525 |
| 2022/0091114 A1* | 3/2022 | Levin | G01N 21/85 |
| 2022/0091115 A1* | 3/2022 | Levin | G01S 19/46 |

OTHER PUBLICATIONS

International Search Report and Written Opinion for PCT/US2021/071510, dated Dec. 29, 2021.

* cited by examiner

*Primary Examiner* — Jonathan M Hansen
(74) *Attorney, Agent, or Firm* — Barnes & Thornburg, LLP

(57) ABSTRACT

A point of use analyte detection and quantification system for aquatic applications is provided. Related methods are also provided.

21 Claims, 20 Drawing Sheets

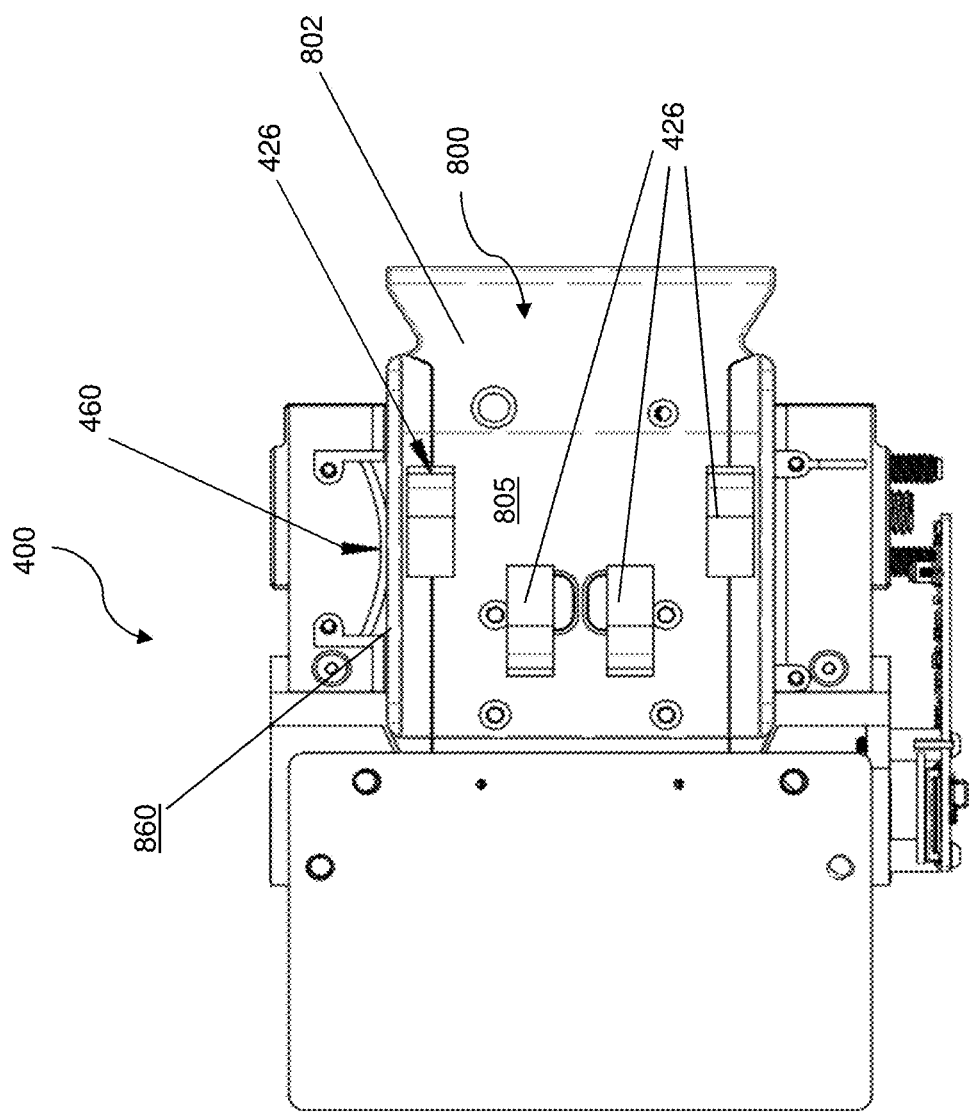

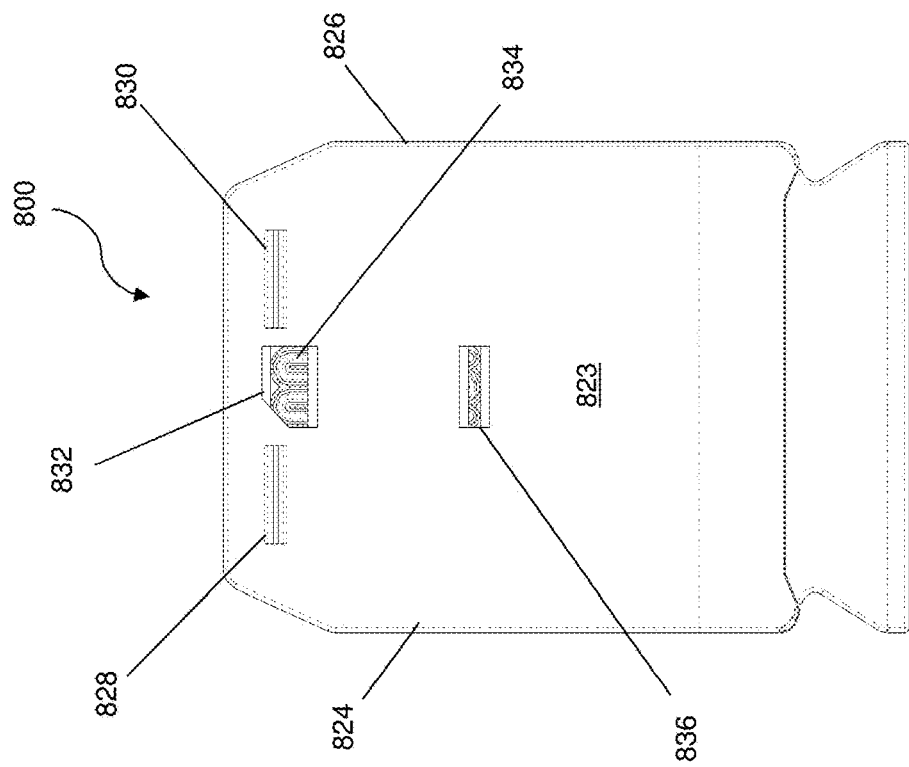
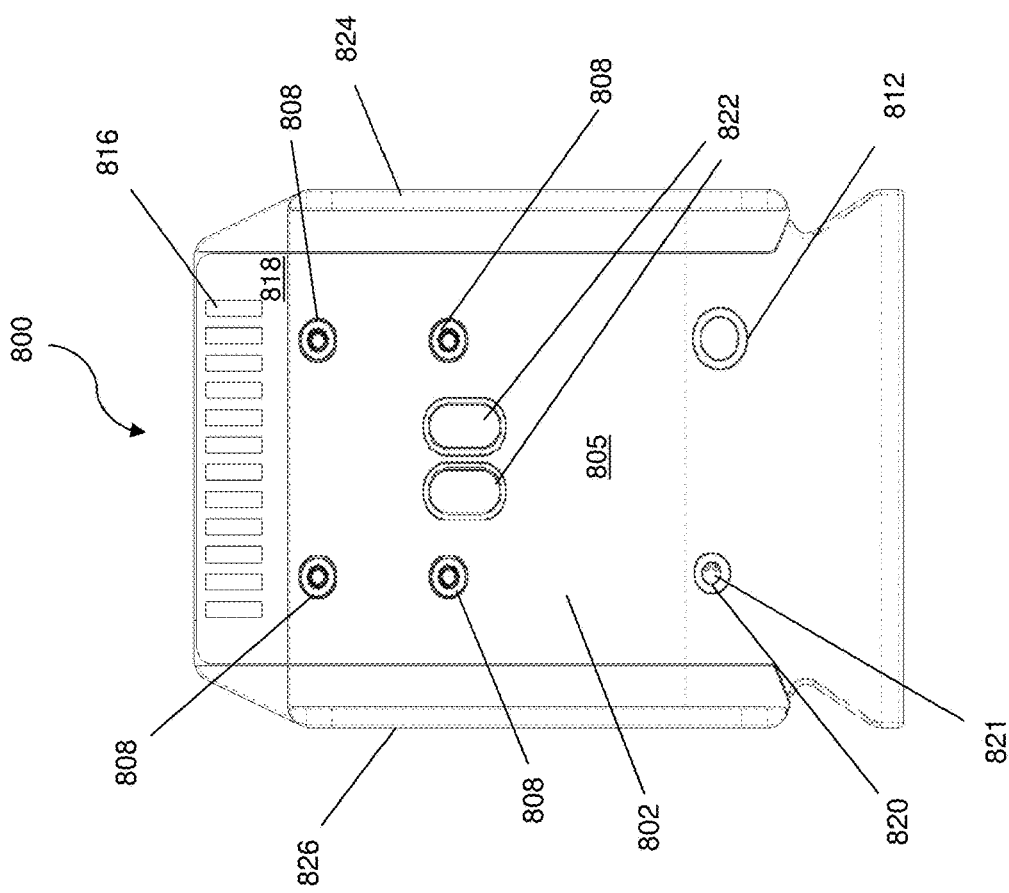

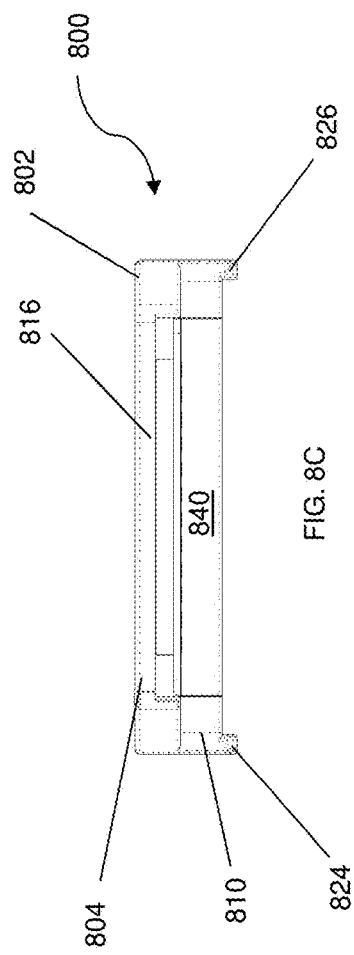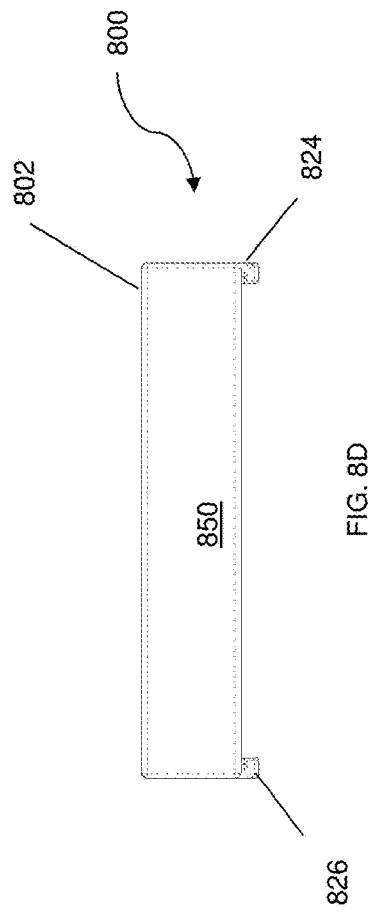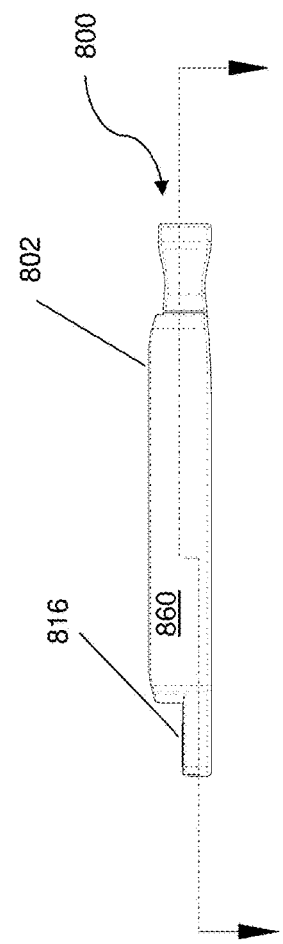

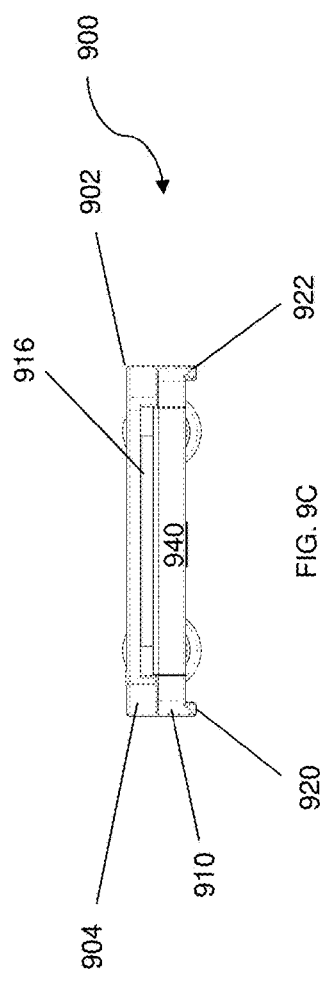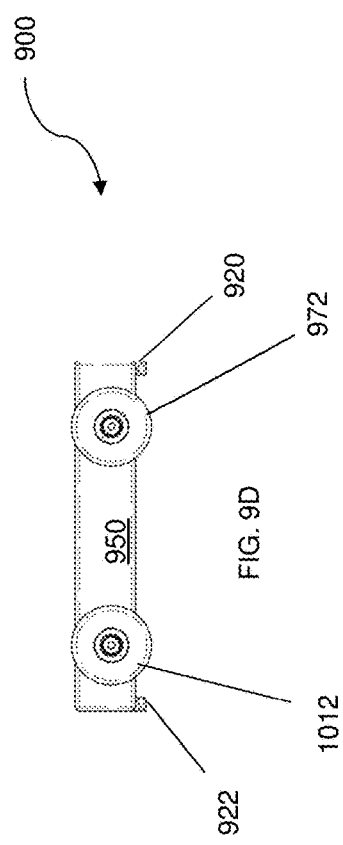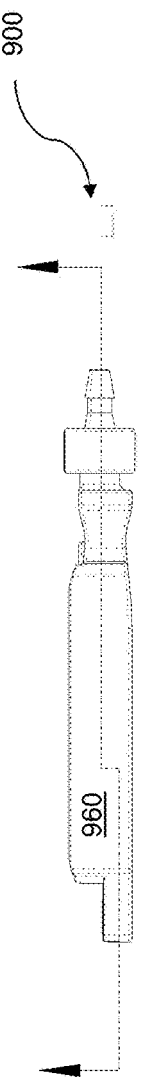

INTERFEROMETRIC DETECTION AND QUANTIFICATION SYSTEM AND METHODS OF USE IN AQUATICS

CROSS-REFERENCE TO RELATED APPLICATIONS

The present application claims priority to U.S. Provisional Application No. 63/080,204, filed Sep. 18, 2020, the content of which is incorporated herein by reference.

BACKGROUND

Microorganisms are of great importance to aquaculture by recycling nutrients, degrading organic matter and infecting and/or killing animals such as fish. Alternatively, some microorganisms may protect fish and larvae against disease. In addition, monitoring for the presence of chemical contaminants and components is equally important to aquaculture and water systems as a whole. Thus, detecting, monitoring, and taking remedial action against the microbial communities, chemical imbalance, or chemical contaminants in aquaculture environments may affect water quality and control the development of microbial infection. There exists a need for rapid, efficient in vitro diagnostic systems that can provide users with information pertaining to qualitative and quantitative data for a variety of pathogens and/or chemicals.

SUMMARY

A portable interferometric system for detection and quantification of analyte within an aquatic test sample composition is provided. The system includes an optical assembly unit, the optical assembly unit comprising a light unit and a detector unit each adapted to fit within a portable housing unit; and a cartridge system adapted to be inserted in the housing and removed after one or more uses, the cartridge system comprising an interferometric chip and a flow cell wafer. The interferometric chip includes one or more waveguide channels having a sensing layer thereon, the sensing layer adapted to bind or otherwise be selectively disturbed by one or more analytes within the aquatic test sample composition.

According to one embodiment, the portable housing is sized and shaped to fit in a user's hand. According to one embodiment, the portable interferometric system further includes at least one display unit. According to one embodiment, the portable interferometric system further includes an external camera, the external camera adapted to capture a photo or video. According to one embodiment, the portable interferometric system includes an alignment means for aligning the cartridge system within a cartridge recess in the interferometric system. According to one embodiment, the sensing layer includes one or more antigens, antibodies, DNA microarrays, polypeptides, nucleic acids, carbohydrates, lipids, or molecularly imprinted polymers, or immunoglobulins suitable for binding one or more analytes within an aquatic test sample composition. According to one embodiment, the portable interferometric system is configured to analyze the light signals from two or more waveguide channels to detect the presence of an analyte that individual waveguides could not have detected alone. According to one embodiment, the one or more waveguide channels each comprises a different sensitive layer to allow the system to detect different analytes on each waveguide channel. According to one embodiment, the sensitive layer is configured to bind one or more chemical, antibody, virus antigen, virus protein, bacteria, fungi, pathogen, RNA, mRNA, plant growth regulator, metal or any combination thereof. According to one embodiment, the portable interferometric system exhibits an analyte detection limit down to about 1.0 picogram/L. According to one embodiment, the portable interferometric system exhibits an analyte detection limit down to about 1000 pfu/ml. According to one embodiment, the portable interferometric system exhibits sensitivity to at least 2 pixels per diffraction line pair. According to one embodiment, the portable interferometric system further includes a location means adapted to determine the physical location of the system. According to one embodiment, the analyte is one or more of a fungicide, herbicide, insecticide, fungus, bacterium, or microbe.

A method of detecting and quantifying the level of analyte in an aquatic test sample composition is provided. The method includes the steps of:
- collecting an aquatic target sample containing one or more analytes;
- optionally entering an identification associated with the target sample;
- introducing the aquatic target sample to an interferometric system as provided herein;
- optionally, mixing the target sample with a buffer solution to form an aquatic test sample composition;
- initiating waveguide interferometry on the test sample composition;
- processing any data resulting from the waveguide interferometry; and
- optionally, transmitting any data resulting from the waveguide interferometry. According to one embodiment, the step of transmitting data includes wirelessly transmitting analyte detection and quantification data to a mobile device or server. According to one embodiment, the method further includes the step of displaying data related to the presence of analyte in the test sample composition on the display unit. According to one embodiment, the aquatic target sample composition is collected from salt or freshwater within or surrounding an aquatic environment. According to one embodiment, the aquatic target sample is collected from a fish farm, effluent system, waterway, water reservoir, potable water source or sanitary sewer. According to one embodiment, the method of detecting and quantifying the level of analyte in an aquatic test sample composition further includes the step of initiating a cleaning or remedial countermeasure against an analyte. According to one embodiment, the aquatic target sample is in the form of, dissolved in, or suspended in a liquid or a gas. According to one embodiment, the data resulting from the waveguide interferometry is provided at or under 30 minutes.

BRIEF DESCRIPTION OF THE DRAWINGS

FIG. 7 illustrates a top view of the optical assembly of FIG. 5A with one embodiment of a cartridge system inserted in the optical assembly.

FIG. 8A illustrates a view of the top surface of one embodiment of a single-use cartridge system.

FIG. 8B illustrates a view of the bottom surface of one embodiment of a single-use cartridge system.

FIG. 8C illustrates a view of the back surface of one embodiment of a single-use cartridge system.

FIG. 8D illustrates a view of the front surface of one embodiment of a single-use cartridge system.

FIG. 8E illustrates view of one side surface of one embodiment of a single-use cartridge system.

FIG. 9C illustrates a view of the back surface of one embodiment of a multi-use cartridge system.

FIG. 9D illustrates a view of the front surface of one embodiment of a multi-use cartridge system.

FIG. 9E illustrates a side surface view of one embodiment of a multi-use cartridge system.

DETAILED DESCRIPTION

Figure 1:
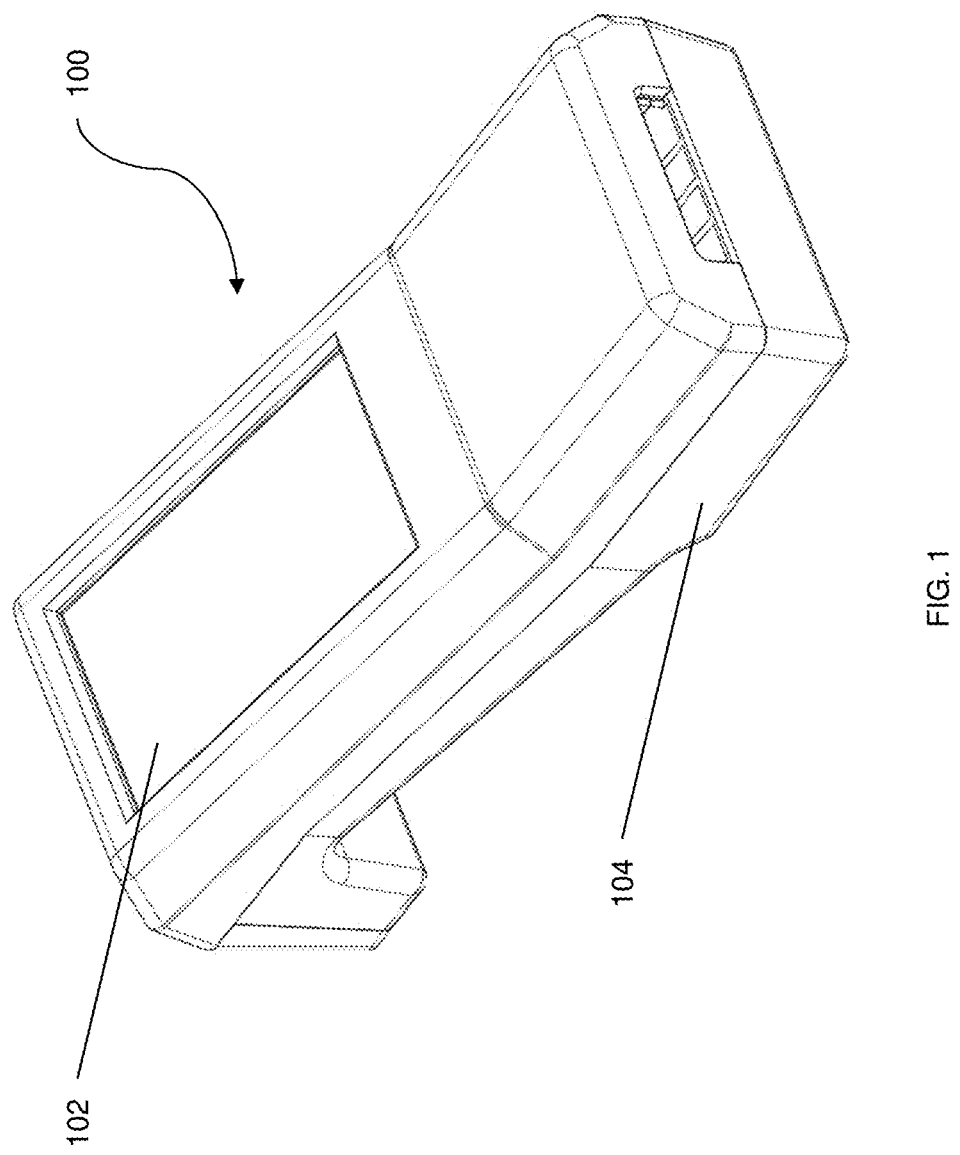
FIG. 1 illustrates a perspective view of one embodiment of a handheld interferometric system as provided herein.

One or more aspects and embodiments may be incorporated in a different embodiment although not specifically described. That is, all aspects and embodiments can be combined in any way or combination. When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

Definitions

As used herein, the term "portable" refers to the capability of the interferometric systems described herein to be transported or otherwise carried to a target sample location for use according the methods provided herein.

As used herein, the term "chemical" refers to a form of matter, natural or synthetic, having constant chemical composition.

As used herein, the term "aquatic" and "aquatic environment" refer to any a water-based environment that is a source for or may harbor analytes provided herein. The water-based environment may be fresh or salt water based. Fresh water examples include, but are not limited to, ponds, lakes, reservoirs, rivers, streams, potable water sources, drainage canals and irrigation canals.

As used herein, the term "aquaculture" refers to the breeding, raising, and harvesting of a living organism in an aquatic environment. The living organism may be a plant, fish, mollusk, crustacean, plant or algae according to one example. A specific example of aquaculture is a fish farm, shrimp farm oyster farm, mariculture, or algaculture (e.g., seaweed) farm.

As used herein, the term "analyte" refers to a substance that is detected, identified, measured or any combination thereof by the systems provided herein. The analyte includes any solid, liquid, or gas affecting (positively or negatively) an environment of interest. The analyte can be beneficial or deleterious. The analyte includes, but is not limited to, chemicals as well as bacteria and other pathogenic microorganisms that may negatively or positively impact animal or plant health or generally infect an aquatic environment. The analyte includes, but is not limited to microbes (beneficial or pathogenic that may be dead or alive), biomarkers, RNA, DNA, pathogen, antigen or portion thereof, antibody, virus, metabolite generated as a reaction to disease or infection, or viral protein. A chemical analyte may include any pesticide, herbicides (e.g., fluridone), insecticides, plant growth regulators, biocides, nutrients, polychlorinated biphenyls (PCB), volatile organic compounds (e.g., benzene, toluene, ethylbenzene and xylenes), tetrachloroethylene (PCE), trichloroethylene (TCE), and vinyl chloride (VC), gasoline, oil, nitrites, or metals. Specific analytes within the aquatic environment include 2,4-D (2,4-dichlorophenoxyacetic acid) and dicamba (2-methoxy-3,6-dichlorobenzoic acid).

As used herein, the term "pathogen," "pathological," "pathological contaminant" and "pathological organism" refer to any toxin (e.g., algal toxin), chemical, bacterium, virus or other microorganism (fungi, protozoa, etc.) that can cause disease for a member of the plant or animal kingdom in an aquatic environment.

As used herein, the terms "sample" and "target sample" all refer to any substance that may be subject to the methods and systems provided herein. Particularly, these terms refer to any matter (animate or inanimate) where an analyte may be present and capable of being detected, quantified, monitored or a combination thereof.

As used herein, the term "point of use" refers to the applicability of the systems provided herein to be utilized by a user at or within the aquatic environment.

"Optional" or "optionally" means that the subsequently described event or circumstance may or may not occur, and that the description includes instances where said event or circumstance occurs and instances where it does not.

As used herein, the term "buffer" refers to a carrier that is mixed with the target sample that includes at least one analyte.

As used herein, the term "test sample composition" refers to the combination of at least one buffer and target sample.

As used herein, the term "aquatic test sample composition" refers to the combination of at least one buffer and target sample taken from an aquatic environment.

As used herein, the term "communication" refers to the movement of air, liquid, mist, fog, buffer, test sample composition, or other suitable source capable of carrying an analyte throughout or within the cartridge system. The term "communication" may also refer to the movement of electronic signals between components both internal and external to the cartridge systems described herein.

As used herein, the term "single-use" refers to the cartridge system being utilized in an interferometric system for a single test or assay before disposal (i.e., not re-used or used for a second time).

As used herein, the term "multiple-use" refers to the cartridge system being utilized for more than one test sample composition (e.g., assay) before disposal.

As used herein, the term "multiplex" refers to the cartridge system being utilized to detect multiple analytes from one target sample composition.

Optical Interferometry Principles

The systems provided include a detector that operates via ultrasensitive, optical waveguide interferometry. The waveguiding and the interferometry techniques are combined to detect, monitor and even measure small changes that occur in an optical beam along a propagation pathway. These changes can result from changes in the length of the beam's path, a change in the wavelength of the light, a change in the refractive index of the media the beam is traveling through, or any combination of these, as shown in Equation 1.

$$\varphi = 2\pi Ln/\lambda \qquad \text{Equation 1}$$

According to Equation 1, $\varphi$ is the phase change, which is directly proportional to the path length, L, and refractive index, n, and inversely proportional to the wavelength ($\lambda$) change. According to the systems and methods provided herein, the change in refractive index is used. Optical waveguides are utilized as efficient sensors for detection of refractive index change by probing near the surface region of the sample with an evanescent field. Particularly, the systems provided herein can detect small changes in an interference pattern.

According to one embodiment, the waveguide and interferometer act independently or in tandem to focus an interferometric diffraction pattern. According to one embodiment, the waveguide, interferometer, and sensor act independently or two parts in tandem, or collectively to focus an interferometric pattern with or without mirrors or other reflective or focal median. According to one embodiment, the waveguide and interferometer exhibit a coupling angle such that focus is at an optimum angle to allow the system to be compact and suited to be portable and handheld.

Interferometric System Overview

The interferometric systems as provided herein are mobile (hand-held) and portable for ease of use in various environments. The interferometric systems include a weight and overall dimensions such that user may hold the entire interferometric system comfortably in one hand. According to one embodiment, the entire interferometric system is under three pounds. Thus, the present disclosure provides a lightweight, handheld and easy-to-use interferometric system that can rapidly, precisely, and accurately provide detection and quantification of analytes in a variety of environments.

The systems as provided herein provide a high throughput modular design. The systems as provided herein may provide both qualitative and quantitative results from one or more analytes within a test sample composition. Particularly, the systems as provided herein may simultaneously provide detection and quantification of one or more analytes from a target sample. According to one embodiment, both qualitative and quantitative results are provided in real-time or near real time.

The interferometric systems provided herein generally include a housing for various detection, analysis and display components. The interferometric system housing includes a rugged, stable, shell or case. The interferometric system housing can withstand hazards of use and cleaning or disinfection procedures of the case surface. The interferometric system housing may be manufactured from a polymer via various techniques such as injection molding or 3D printing. The interferometric system housing may be manufactured to include a coloration that provides the interferometric system housing with a particular color or color scheme.

According to one embodiment, the interferometric systems provided herein include components that are sealed, waterproof or water resistant to the outside environment to minimize opportunities for contamination of a target sample. The overall arrangement of components within the interferometric systems minimize harboring of contamination in any hard-to-reach areas allowing for ease of disinfection.

The interferometric systems provided herein include a cartridge system. The cartridge systems provided herein integrate with one or more independent or integrated optical waveguide interferometers. The cartridge systems provide efficient sample composition communication through a microfluidic system mounted on or within the cartridge housing. The cartridge is suitable for one or more analytes to be detected in a single sample in a concurrent, simultaneous, sequential or parallel manner. The cartridge systems provided herein may be utilized to analyze in a multiplex manner. That is, one test sample composition will be tested to determine the presence of multiple analytes at the same time by utilizing a plurality of waveguide channels that interact with the test sample composition.

The cartridge systems provided herein are easily removable and disposable allowing for overall quick and efficient use without the risk of cross-contamination from a previous target sample. The cartridge may be safely disposed of after a single use. Disposal after a single use may reduce or eliminate user exposure to biological hazards. According to one embodiment, the cartridge system includes materials that are biodegradable, or recycled materials, to reduce environmental impact. The cartridge system may be cleaned and re-used or otherwise recycled after a single use.

The cartridge system as provided herein may be suited for multiple or one-time use. The single-use cartridge system may be manufactured in a manner such that a buffer solution is pre-loaded in the microfluidic system. By providing the buffer solution pre-loaded in the single-use cartridge system, gas bubbles are reduced or otherwise eliminated. After a single use, the entire cartridge system is safely discarded or recycled for later use after cleaning. Put another way, after introduction and detection of a test sample composition, the entire single-use cartridge system is not used again and, instead, discarded.

The cartridge systems as provided herein may be suited for multiple uses. According to such an embodiment, the cartridge system may be used one or more times prior to the cartridge system being safely discarded or recycled. The cartridge system may also be cleaned and re-used or otherwise recycled after multiple uses. According to one embodiment, the cartridge system facilitates cleaning and re-tooling to allow the cartridge system to be replenished and returned to operation.

According to one embodiment, the interferometric systems as provided herein have an analyte detection limit down to about 10 picogram/ml. According to one embodiment, the systems as provided herein have an analyte detection limit down to about 1.0 picogram/ml. According to one embodiment, the systems as provided herein have an analyte detection limit down to about 0.1 picogram/ml. According to one embodiment, the systems as provided herein have an analyte detection limit down to about 0.01 picogram/ml.

According to one embodiment, the interferometric systems as provided herein have an analyte detection limit down to about 3000 plaque forming units per milliliter (pfu/ml). According to one embodiment, the systems as provided herein have an analyte detection limit down to about 2000 pfu/ml. According to one embodiment, the systems as provided herein have an analyte detection limit down to about 1000 pfu/ml. According to one embodiment, the systems as provided herein have an analyte detection limit down to about 500 plaque forming units per milliliter (pfu/ml). According to one embodiment, the systems as provided herein have an analyte detection limit down to about 100 plaque forming units per milliliter (pfu/ml). According to one embodiment, the systems as provided herein have an analyte detection limit down to about 10 plaque forming units per milliliter (pfu/ml). According to one embodiment, the systems as provided herein have an analyte detection limit down to about 1 plaque forming units per milliliter (pfu/ml). According to one embodiment, the systems as provided herein have an analyte detection limit to about 1 plaque forming units per liter (pfu/l).

According to one embodiment, the interferometric systems provided herein provide both qualitative and quantitative results at or under 60 minutes after sample introduction to the system. According to one embodiment, both qualitative and quantitative results are provided at or under 30 minutes. According to one embodiment, both qualitative and quantitative results are provided at or under 10 minutes. According to one embodiment, both qualitative and quantitative results are provided at or under 5 minutes. According to one embodiment, both qualitative and quantitative results are provided at or under 2 minutes. According to one embodiment, both qualitative and quantitative results are provided at or under 1 minute.

The interferometric systems as provided herein may be powered via alternating current or direct current. The direct current may be provided by a battery such as, for example, one or more lithium or alkaline batteries. The alternating or direct current may be provided by alternative energy sources such as wind or solar.

According to one embodiment, the interferometric system is stabilized to address vibrational distortions. The system may be stabilized by various means including mechanical, chemically (fluid float or gel pack), computer-assisted system (electronically), or digitally (e.g., via a camera). In some implementations, the systems provided herein allow for point of use assays that are stable in various conditions, including ambient temperature and humidity as well as extreme heat, cold and humidity.

The interferometric systems as provided herein may be equipped with one or more software packages loaded within. The software may be electronically connected to the various system components as provided herein. The software may also be electronically integrated with a display for viewing by a user. The display may be any variety of display types such as, for example, a LED-backlit LCD. The system may further include a video display unit, such as a liquid crystal display ("LCD"), an organic light emitting diode ("OLED"), a flat panel display, a solid state display, or a cathode ray tube ("CRT").

According to one embodiment, the interferometric system as provided herein may interface with or otherwise communicate with a transmission component. The transmission component may be in electronic signal communication with both the cartridge system and interferometric system components. The transmission component sends or transmits a signal regarding analyte detection data and quantification data. The transmission of such data may include real-time transmission via any of a number of known communication channels, including packet data networks and in any of a number of forms, including instant message, notifications, emails or texts. Such real-time transmission may be sent to a remote destination via a wireless signal. The wireless signal may travel via access to the Internet via a surrounding Wi-Fi network. The wireless signal may also communicate with a remote destination via Bluetooth or other radio frequency transmission. The remote destination may be a smart phone, pad, computer, cloud device, or server. The server may store any data for further analysis and later retrieval. The server may analyze any incoming data using artificial intelligence learning algorithms or specialized pathological, physical, or quantum mechanical expertise programmed into the server and transmit a signal.

According to one embodiment, the transmission component may include a wireless data link to a phone line. Alternatively, a wireless data link to a building Local Area Network may be used. The system may also be linked to Telephone Base Unit (TBU) which is designed to physically connect to a phone jack and to provide 900 MHz wireless communications thereby allowing the system to communicate at any time the phone line is available.

According to one embodiment, the interferometric system may include a location means. Such a location means includes one or more geolocation device that records and transmits information regarding location. The location means may be in communication with a server, either from a GPS sensor included in the system or a GPS software function capable of generating the location of the system in cooperation with a cellular or other communication network in communication with the system. According to a particular embodiment, the location means such as a geolocation device (such as GPS) may be utilized from within its own device or from a mobile phone or similarly collocated device or network to determine the physical location of the cartridge system.

According to one embodiment, the interferometric system contains a geo-location capability that is activated when a sample is analyzed to "geo-stamp" the sample results for archival purposes. According to one embodiment, the interferometric system contains a time and date capability that is activated when a sample is analyzed to time stamp the sample results for archival purposes.

The interferometric systems provided herein may interface with software that can process the signals hitting the detector unit. The cartridge system as provided herein may include a storage means for storing data. The storage means is located on or within the cartridge housing or within the interferometric system housing. The storage means communicates directly with electronic components of the interferometric system. The storage means is readable by the interferometric system. Data may be stored as a visible code or an index number for later retrieval by a centralized database allowing for updates to the data to be delivered after the manufacture of the cartridge system. The storage means may include memory configured to store data provided herein.

The data retained in the storage means may relate to a variety items useful in the function of the interferometric system. According to a particular embodiment, the data may provide the overall interferometric system or cartridge system status such as whether the cartridge system was previously used or is entirely new or un-used. According to a particular embodiment, the data may provide a cartridge system or interferometric system identification. Such an identification may include any series of letter, numbers, or a combination thereof. Such identification may be readable through a QR code. The identification may be alternatively memorialized on a sticker located on the cartridge housing or interferometric system housing. According to one embodiment, the cartridge housing contains a bar code or QR code. According to one embodiment, the cartridge system contains a bar code or QR code for calibration or alignment. According to one embodiment, the cartridge system contains a bar code or QR code for identification of the cartridge or test assay to be performed. According to one embodiment, the cartridge system contains a bar code or QR code for identification of the owner and location of where any data generated should be transmitted. A user may scan such a QR code with the interferometric system's external camera prior to use to use of the system such that identification and transmission may occur (e.g., automatically or upon user direction).

According to a particular embodiment, the data retained in the storage means may provide the number of uses remaining for a multiple-use cartridge system. According to a particular embodiment, the data may provide calibration data required by interferometric system to process any raw data into interpretable results. According to a particular embodiment, such data may relate to information about the analyte and any special processing instructions that can be utilized by the cartridge system to customize the procedure for the specific combination of receptive surface(s) and analyte(s). The interferometric system as provided herein may include electronic memory to store data via a code or an index number for later retrieval by a centralized database allowing for updates to the data to be delivered after the manufacture of the cartridge system.

The interferometric system may include a memory component such that operating instructions for the interferometric system may be stored. All data may be stored or archived for later retrieval or downloading onto a workstation, pad, smartphone or other device. According to one embodiment, any data obtained from the system provided herein may be submitted wirelessly to a remote server. The interferometric system may include logic stored in local memory to interpret the raw data and findings directly, or the system may communicate over a network with a remotely located server to transfer the raw data or findings and request interpretation by logic located at the server. The interferometric system may be configured to translate information into electrical signals or data in a predetermined format and to transmit the electrical signals or data over a wireless (e.g., Bluetooth) or wired connection within the system or to a separate mobile device. The interferometric system may perform some or all of any data adjustment necessary, for example adjustments to the sensed information based on analyte type or age, or may simply pass the data on for transmission to a separate device for display or further processing.

The interferometric systems provided herein may include a processor, such as a central processing unit ("CPU"), a graphics processing unit ("GPU"), or both. Moreover, the system can include a main memory and a static memory that can communicate with each other via a bus. Additionally, the system may include one or more input devices, such as a keyboard, touchpad, tactile button pad, scanner, digital camera or audio input device, and a cursor control device such as a mouse. The system can include a signal generation device, such as a speaker or remote control, and a network interface device.

According to one embodiment, the interferometric system may include color indication means to provide a visible color change to identify a particular analyte. According to one embodiment, the system may include a reference component that provides secondary confirmation that the system is working properly. Such secondary confirmation may include a visual confirmation or analyte reference that is detected and measured by the detector.

The interferometric system as provided herein may also include a transmitting component. The transmitting component may be in electronic signal communication with the detector component. The transmitting component sends or transmits a signal regarding analyte detection and quantification data. The transmission of such data may include real-time transmission via any of a number of known communication channels, including packet data networks and in any of a number of forms, including text messages, email, and so forth. Such real-time transmission may be sent to a remote destination via a wireless signal. The wireless signal may travel via access to the Internet via a surrounding Wi-Fi network. The wireless signal may also communicate with a remote destination via Bluetooth or other radio frequency transmission. The remote destination may be a smart phone, pad, computer, cloud device, or server. The server may store any data for further analysis and later retrieval. The server may analyze any incoming data using artificial intelligence learning algorithms or specialized pathological, physical, or quantum mechanical expertise programmed into the server and transmit a signal.

According to one embodiment, the interferometric system includes a wireless data link to a phone line. Alternatively, a wireless data link to a building Local Area Network may be used. The system may also be linked to Telephone Base Unit (TBU) which is designed to physically connect to a phone jack and to provide 900 MHz wireless communications thereby allowing the system to communicate at any time the phone line is available.

According to one embodiment, the system may also include geolocation information in its communications with the server, either from a GPS sensor included in the system or a GPS software function capable of generating the location of the system in cooperation with a cellular or other communication network in communication with the system. According to a particular embodiment, the system may include a geolocation device (such as GPS or RFID) either from within its own device or from a mobile phone or similarly collocated device or network to determine the physical location of the system.

According to one embodiment, the interferometric system includes an external camera. The external camera may be at least partially located within the interferometric system housing but include a lens exposed to the exterior of the housing such that the external camera may take photos and video of a target sample prior to collection (e.g., soil, plant, etc.). The external camera may capture video or images that aid in the identification of an analyte and confirmation of the resulting data. The external camera may also capture video images that aid in selecting a proper remedial measure. The external camera may capture video or images that aid in the identification of a target sample or source thereof.

The external camera may capture video or images in connection with scanning and identifying a QR code (such as a QR code on an external surface of a cartridge housing). When located on an external surface of the cartridge housing, the QR code may also aid in identifying ownership of generated data and transmission of such data to a correct owner.

According to one embodiment, the cartridge system contains a geo-location capability that is activated when a sample is analyzed to "geo-stamp" the sample results for archival purposes. According to one embodiment, the cartridge system contains a time and date capability that is activated when a sample is analyzed to time stamp the sample results for archival purposes. According to one embodiment, the cartridge system includes materials that are biodegradable, or recycled materials, to reduce environmental impact. Any used cartridge system provided herein may be disposed of in any acceptable manner such as via a standard biohazard container. According to one embodiment, the cartridge system facilitates cleaning and re-tooling to allow the cartridge system to be replenished and returned to operation.

According to one embodiment, the cartridge system is stabilized to address vibrational distortions. The system may be stabilized by various stabilization means including mechanical (alignment means as provided herein), chemically (fluid float or gel pack), computer-assisted system (electronically), or digitally (e.g., via a camera or digital processing).

Microfluidic System Overview—Single-Use Cartridge System

The single-use cartridge system provided herein includes a microfluidic system for communicating or otherwise providing a means for test sample and buffer to mix thereby resulting in a test sample composition. The microfluidic system causes the test sample composition move through the detection region to allow for detection and analysis of one or more analytes. The microfluidic system includes an injection port for introduction of a test sample. The injection port may optionally include a check valve. The microfluidic system further includes a first microchannel section having a first end attached in communication with the injection port check valve and a second end in communication with a mixing bladder. According to one embodiment, the first microchannel section contains a filter to remove materials not capable of detection and quantification. The mixing bladder is sized, shaped and otherwise configured to store buffer. The mixing bladder is sized, shaped and otherwise configured to aid in mixing buffer and test sample to form the test sample composition. The mixing bladder may be bypassed such that the test sample composition may be automatically discharged or allowed to proceed through the microfluidic system. The mixing bladder may include a temperature control means in the form of a metal coil wrapped around the mixing bladder such that the temperature control means is heated upon introduction of an electric current.

The microfluidic system further includes second microchannel section having a first end attached in communication with the mixing bladder and a second end attached in communication with a flow cell having at least one detection microchannel. By including multiple two or more detection microchannels, the cartridge system is particularly suited for high throughput and improved testing efficiency by being able to detect and quantify analyte in more than one test sample composition.

The microfluidic system further includes at least one pump. Suitable pumps include micropumps such as, but are not limited to, diaphragm, piezoelectric, peristaltic, valve-less, capillary, chemically-powered, or light-powered micropumps. According to an alternative embodiment, the microfluidic system further includes at least one pump that is a, positive-displacement pump, impulse pump, velocity pump, gravity pump, steam pump, or valve-less pump of any appropriate size. According to a single-use embodiment of the cartridge system, the cartridge system contains at least one pump located within the cartridge housing. According to one embodiment of a single-use cartridge system, the pump overlays or otherwise engages or touches the first microchannel section, second microchannel section and mixing bladder.

The microfluidic system of the single-use cartridge system as provided herein may be manufactured and packaged under negative pressure or vacuum sealed. In this manner, the negative pressure allows for a test sample to be pulled in and become self-loading upon introduction of the test sample. The negative pressure further allows for a test sample to be pulled in in the microfluidic system to reduce, avoid or eliminate bubble formation upon introduction of the test sample. According to an alternative embodiment, the microfluidic system is manufactured and packaged under a positive pressure. According to either embodiment, the microfluidic system of a single-use cartridge system may be pre-loaded with a buffer solution at the time of manufacture. The buffer may be custom designed or designated for a particular analyte detection. Buffer solution that is used (i.e., buffer waste) and resulting test sample composition waste may be contained permanently in the single-use cartridge system.

According to one embodiment, the pump can be powered by a battery or electricity transferred from the testing device. Alternatively, the energy to power the pump can be mechanically transferred by direct force, electromagnetic induction, magnetic attraction, audio waves, or piezo electric transfer. According to one embodiment, the cartridge system includes at least one pulse dampening component such as a regulator or accumulator or bladder.

Microfluidic System Overview—Multiple-Use Cartridge System

The multiple-use cartridge system provided herein includes a microfluidic system for communicating or otherwise providing a means for a test sample composition to move through the cartridge system and allow for detection and analysis of one or more analytes. According to a particular embodiment, the test sample and test sample composition are air or liquid. An ingress port is located on a front surface of the multiple-use cartridge system. The ingress port is in communication with a first microchannel section having a first end attached in communication with an ingress port check valve and a second end in communication with second microchannel section. A filter may be located anywhere within the first microchannel section.

The second microchannel section includes a first end in communication the first microchannel section and a second end in communication with a flow cell having at least one detection microchannel. The cartridge system includes a detection region that accommodates or is otherwise adapted to receive the chip and flow cell wafer.

The detection microchannel is in communication with a first end of a third microchannel section. The third microchannel section includes a flow electrode to approximate flow rate and is correlated with measured impedance. The third microchannel section includes a second end in communication with the first end of a fourth microchannel. The fourth microchannel includes a second end in communication with a check valve which, in turn, is in communication with an egress port. The chip utilized in the multiple-use embodiment may be removable from the cartridge system.

The microfluidic system further includes at least one pump. Suitable pumps include micropumps that include, but are not limited to, diaphragm, piezoelectric, peristaltic, valveless, capillary, chemically-powered, or light-powered micropumps. According to an alternative embodiment, the microfluidic system further includes at least one pump that is a positive-displacement pump, impulse pump, velocity pump, gravity pump, steam pump, or valve-less pump of any appropriate size. According to one multiple-use embodiment of the cartridge system, the cartridge system contains at least one pump located outside (external to) the cartridge housing but in communication with the microfluidic system. The external pump may be utilized to move test sample composition through the microfluidic system to aid in removal of air or bubble that may be present in a liquid test sample composition prior to use. According to one embodiment, the cartridge system contains at least one pump dampening device.

All of the cartridge systems provided herein may utilize the pump to manipulate the communication of test sample composition throughout the microfluidic system. According to one embodiment, the pump causes or otherwise aids movement of test sample composition through the microchannels as well as the mixing bladder, when present.

Handheld Interferometric System—Exemplary Embodiment

FIG. 1 illustrates a perspective view of one embodiment of a portable interferometric system 100 as provided herein. The portable interferometric system 100 may include a display unit 102. The portable interferometric system 100 may include a housing 104 adapted to fit within a user's hand.

Figure 2A:
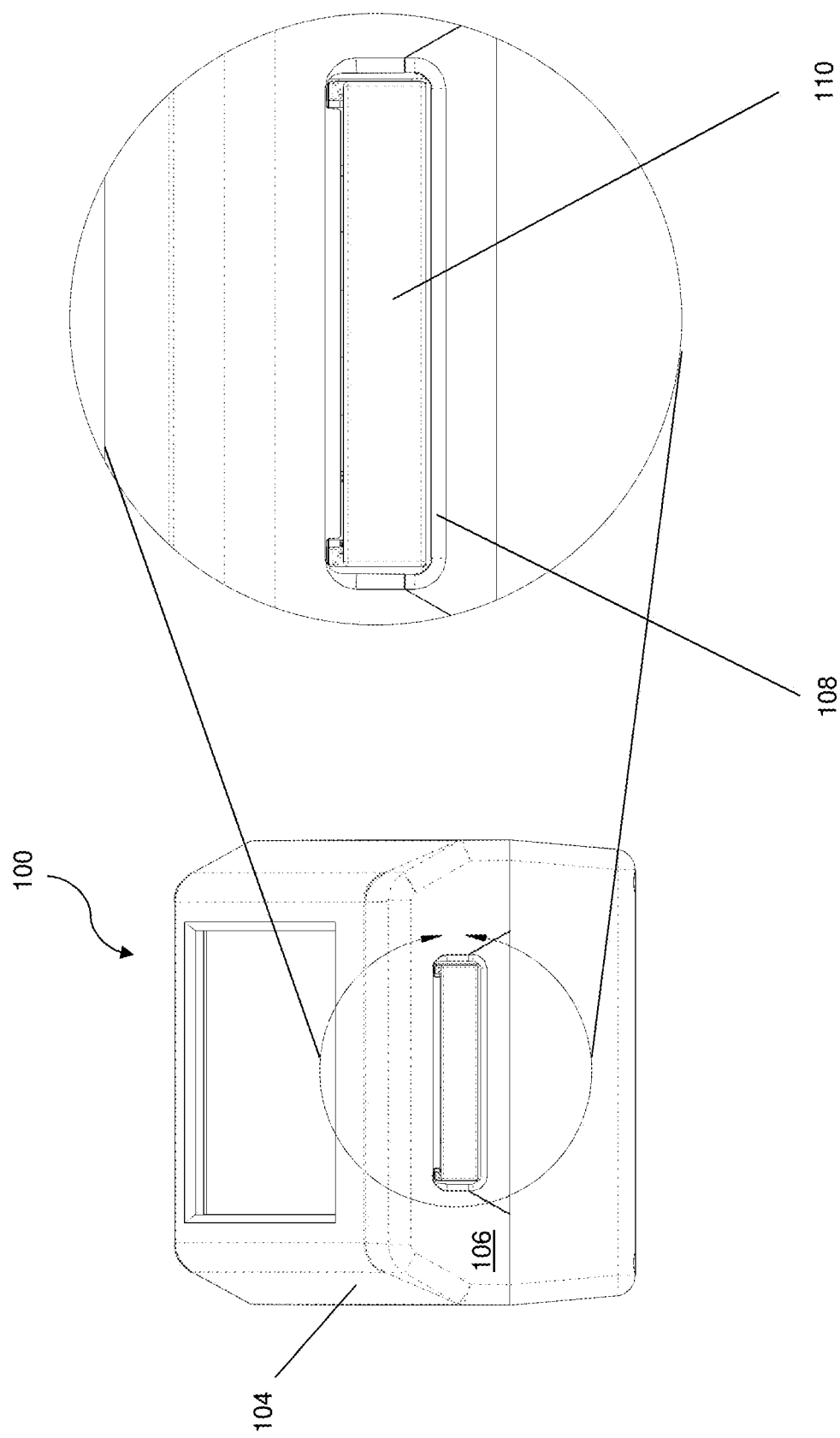
FIG. 2A illustrates a front view of one embodiment of a handheld interferometric system as provided herein.

FIG. 2A illustrates a front view of one embodiment of a portable interferometric system 100 that utilizes the cartridge systems provided herein. The housing 104 includes an external front surface 106 defining an opening 108 adapted to receive the cartridge system provided herein. The opening 108 aids in the alignment and proper position of the cartridge system as provided herein within the handheld interferometric system 100. The opening 108 may optionally include a flap 110 that shields or covers the opening 108 when the cartridge is not inserted. The flap 110 may be hinged on any side so as to aid in the movement of the flap 110 from a first, closed position to a second, open position upon insertion of the cartridge system.

Figure 2B:
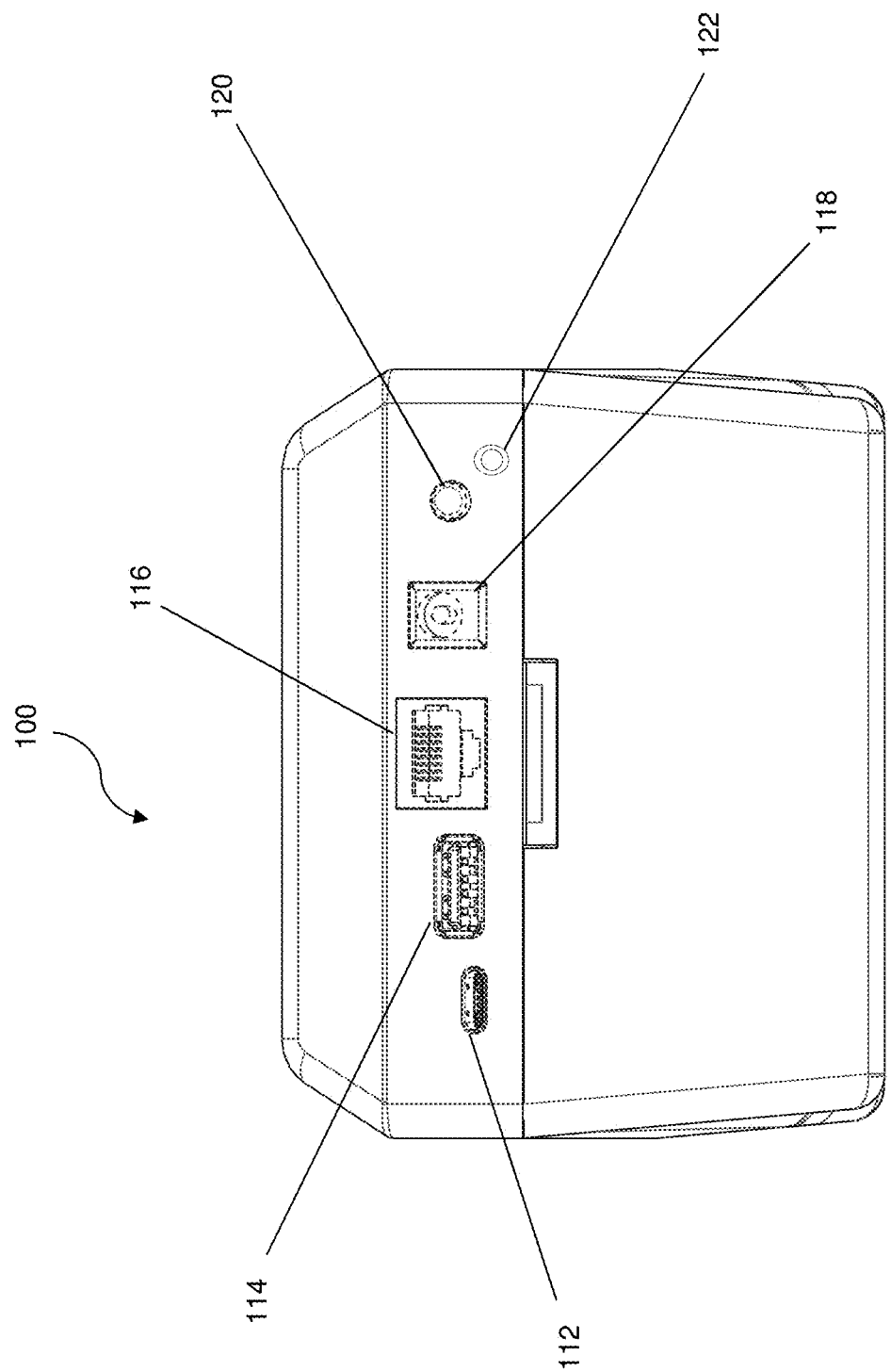
FIG. 2B illustrates a rear view of one embodiment of a handheld interferometric system as provided herein.

FIG. 2B illustrates a rear view of one embodiment of a portable interferometric system 100 as provided herein. The housing 104 is adapted to include USB Type C 112, USB Type A 114, data or phone line inlet 116, power cord inlet 118, power switch 120, and external camera or other light sensitive device 122.

Chip Overview

As previously noted, the cartridge systems provided herein further includes a detection region. This detection region accommodates or is otherwise adapted to receive an interferometric chip and flow cell wafer. The flow cell wafer includes at least one detection microchannel. The flow cell wafer is located directly above the chip. The detection microchannel may be etched onto a flow cell wafer having a substantially transparent or clear panel or window. The detection microchannel aligns with each waveguide channel in the chip.

In use, a light signal may be emitted from a light unit located in the interferometric system. The light enters flow through entry gradients in the chip and through one or more waveguide channels. According to a particular embodiment, there may be two or more waveguides channels to determine the presence of a separate analyte that each of the individual waveguides channels alone would not have been able to identify alone. The evanescent field is created when the light illuminates the waveguide channel. The light signal is then directed by exit gradients to a detector unit such as a camera unit. The detector unit is configured to receive the light signal and detect an analyte present in a test sample composition. The chip may further include a reference waveguide channel.

A sensing layer is adhered to a top side of one or more waveguide channels. According to a particular embodiment, the sensing layer may include one or more antigens or antibodies that are immobilized on the waveguide channel surface to sense the antigen-specific antibody or antigen, respectively. According to another embodiment, the sensing layer may include envelope, membrane, nucleocapsid N-proteins or different domains of one of the proteins in a natural or artificial virus used to delivery interfering RNA (RNAi) as a treatment.

According to a particular embodiment, the sensing layer may include a molecularly imprinted polymer. The molecularly imprinted polymer leaves cavities in the polymer matrix with an affinity for a particular analyte such as an antibiotic.

According to a particular embodiment, the sensing layer may include a DNA microarray of DNA probes. Each probe may be specific for a pathogen (i.e., bacterial species) and when the probe hybridizes with a sample, the sample/probe complex fluoresces in UV light or may be detected via interferometric analysis.

According to one embodiment, the sensing layer may utilize immunoassays on top of the waveguide channels for detection of one or more analytes. According to one embodiment, the system may include, or function based on, an enzyme-linked immunosorbent assay (ELISA) or other ligand binding assays that detect analytes in target samples. According to one embodiment, the sensing layer may utilize one or more polypeptides, nucleic acids, antibodies, carbohydrates, lipids, receptors, or ligands of receptors, fragments thereof, and combinations thereof. According to one such embodiment, the sensing layer is configured to include one or more antibodies as well as one or more immunoglobulins to aid in the indication of the stage of analyte infection. Suitable immunoglobulins include IgG, IgM, IgA, IgE and IgD.

Flow Cell Overview

Each of the cartridge systems described herein include a flow cell having at least one detection microchannel adapted to communicate with one or more test sample compositions flowing through a waveguide channel in a chip beneath the flow cell. According to one embodiment, the cartridge systems may include at least two, at least three, or at least four detection microchannels with each detection microchannel adapted to communicate one or more test sample composition allowing detection of the same or different analytes.

Each detection microchannel is located on or within a flow cell manufactured from a wafer. The at least one detection microchannel may be etched, molded or otherwise engraved into one side of the flow cell wafer. Thus, the at least one detection microchannel may be shaped as a concave path as a result of the etching or molding within the flow cell wafer.

The flow cell wafer is oriented above the chip during use such that the detection microchannel may be orientated or otherwise laid out in variety of flow patterns above the waveguide channels. The detection microchannel may be laid out, for example, in a simple half loop flow pattern, serial flow pattern, or in a serpentine flow pattern. The serpentine flow pattern is particularly suited for embodiments where there are multiple waveguide channels that are arranged in a parallel arrangement. By utilizing the serpentine flow pattern, the test composition flows consistently over the waveguide channels without varying flow dynamics.

Chip, Flow Cell and Optical Assembly—Exemplary Embodiment

Figure 3A:
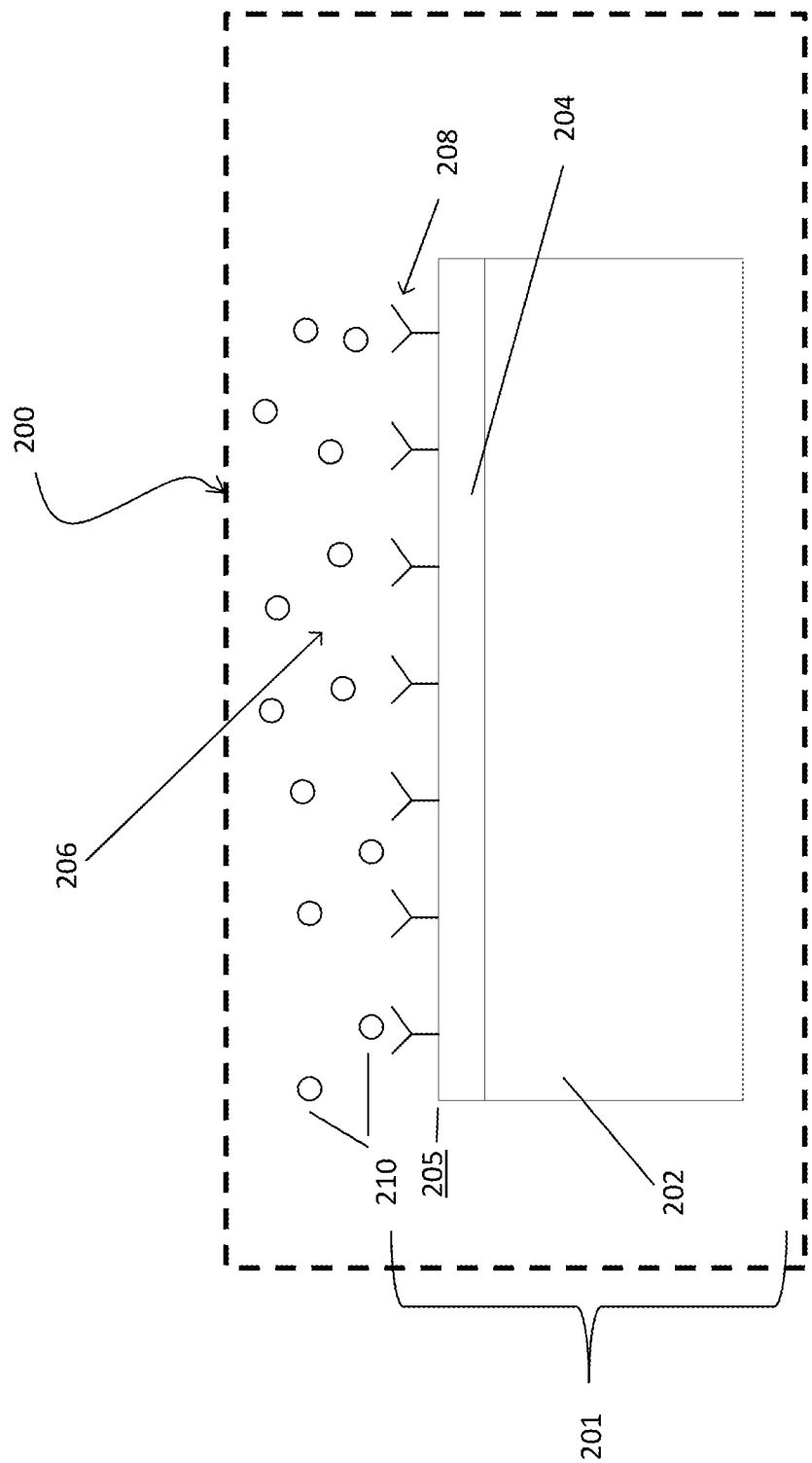
FIG. 3A illustrates a cross-sectional view of an interferometric chip that may be integrated into a cartridge system as provided herein.

FIG. 3A illustrates a cross-sectional view of an optical detection region 200 of a cartridge system. A chip (or substrate) 202 includes a waveguide channel 204 attached to a surface 205 (such as the illustrated top surface) of the chip 202. An evanescent field 206 is located above the waveguide channel 204. A sensing layer 208 is adhered to a top side of the waveguide channel 204. As illustrated, antibodies 210 are shown that may bind or otherwise immobilized to the sensing layer 208, however, the sensing layer 208 may be adapted to bind any variety of analytes. As such, adjusting or otherwise modifying the sensing layer 208 allows for the cartridge system to be utilized for multiple different types of analytes without having to modify the cartridge system or and surrounding interferometric system components. In general use, an light signal (e.g., laser beam) illuminates the waveguide channel 204 creating the evanescent field 206 that encompasses the sensing layer 208. Binding of an analyte impacts the effective index of refraction of the waveguide channel 204.

Figure 3B:
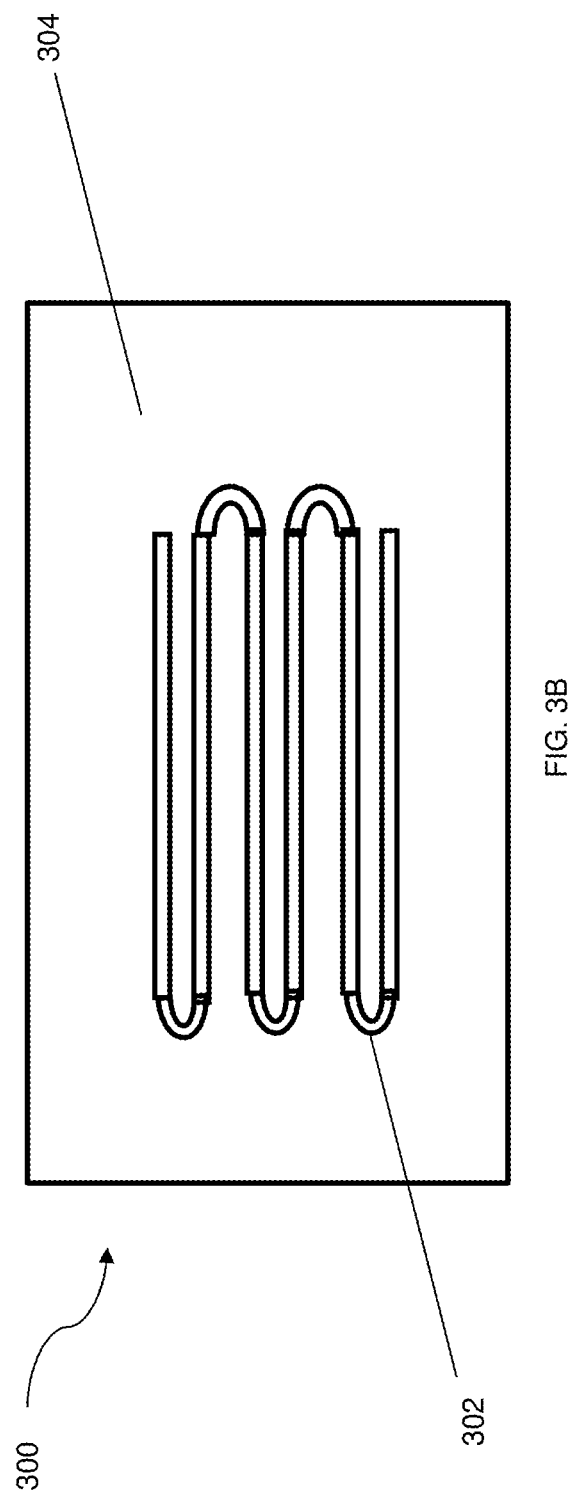
FIG. 3B illustrates a bottom view of a flow cell wafer having a serpentine shaped detection microchannel.

A bottom view of an exemplary flow cell 300 is illustrated in FIG. 3B. At least one detection microchannel 302 is located on or within a flow cell 300 manufactured from a transparent wafer. The at least one detection microchannel 302 may be etched, molded or otherwise engraved into one side of the flow cell wafer 304. Thus, the at least one detection microchannel 302 may be shaped as a concave path as a resulted of the etching or molding within the flow cell wafer 304. The flow cell wafer 304 may be manufactured a material such as opaque plastic, or other suitable material. The flow cell wafer 304 may optionally be coated with an anti-reflection composition.

Figure 3C:
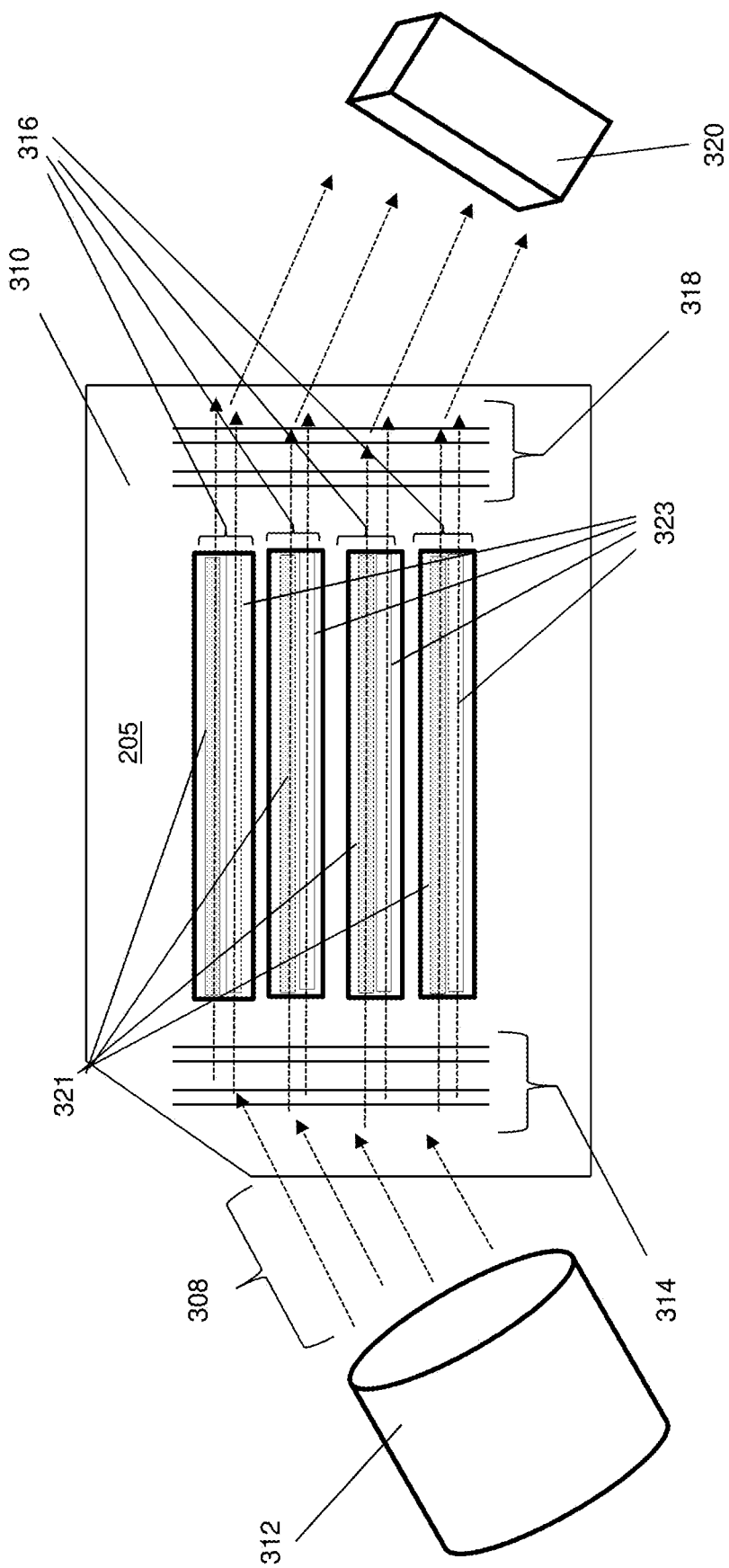
FIG. 3C illustrates a top view of a chip illustrating the movement of an light signal through the chip.

The movement of an light signal 308 (series of arrows) through a chip 310 is illustrated in FIG. 3C. The light signal 308 moves from a light unit 312, such as a laser unit, through a plurality of entry gradients 314 and through one or more waveguide channels 316. Each channel includes a pair of waveguides (321, 323). One of the pair of waveguides 321 is coated with a sensing layer 208 (as indicated by shading in FIG. 3C). The other one of the pair of waveguides 323 is not coated with the sensing layer 208 (serving as a reference). The combination of the light from each in the pair of waveguides (312, 323) create an interference pattern which is illuminated on detector unit 320.

According to a particular embodiment, the two or more waveguides channels 316 are utilized that are able to determine the presence of an analyte that each of the individual waveguides channels 316 alone would not have been able to identify alone. The light signal 308 is then directed by exit gradients 318 to a detector unit 320 such as a camera unit.

The detector unit 320 is configured to receive the light signal 308 and detect any analyte present in a target sample composition flowing through the detection microchannel 302 (see FIG. 3B).

The chip 310 includes a combination of substrate 202 (see FIG. 3A), waveguide channel (see FIG. 3A part 204 and FIG. 3C part 316) and sensitive layer 208 (see FIG. 3A). The flow cell 300 is oriented above the top surface 205 of the chip 310 during use such that the detection microchannel 302 may be orientated or otherwise laid out in variety of flow patterns above the waveguide channels 316. The detection microchannel 302 may be laid out, for example, in a simple half loop flow pattern, serial flow pattern, or in a serpentine flow pattern as illustrated in FIG. 3B. The serpentine flow pattern is particularly suited for embodiments where there are multiple waveguide channels 316 that are arranged in a parallel arrangement (see FIG. 3C). By utilizing the serpentine flow pattern, the test composition flows consistently over the waveguide channels 316 without varying flow dynamics.

The light signal passes through each waveguide channel as illustrated in FIG. 3C, may combine thereby forming diffraction patterns on the detector unit. The interaction of the analyte 210 (see FIG. 3A) and the sensing layer 208 changes the index of refraction of light in the waveguide channel per Equation 1. The diffraction pattern is moved which is detected by the detector unit. The detector unit as provided herein may be in electronic communication with video processing software. Any diffraction pattern movement may be reported in radians of shift. The processing software may record this shift as a positive result. The rate of change in radians that happens as testing is conducted may be proportional to the concentration of the analyte.

Figure 4:
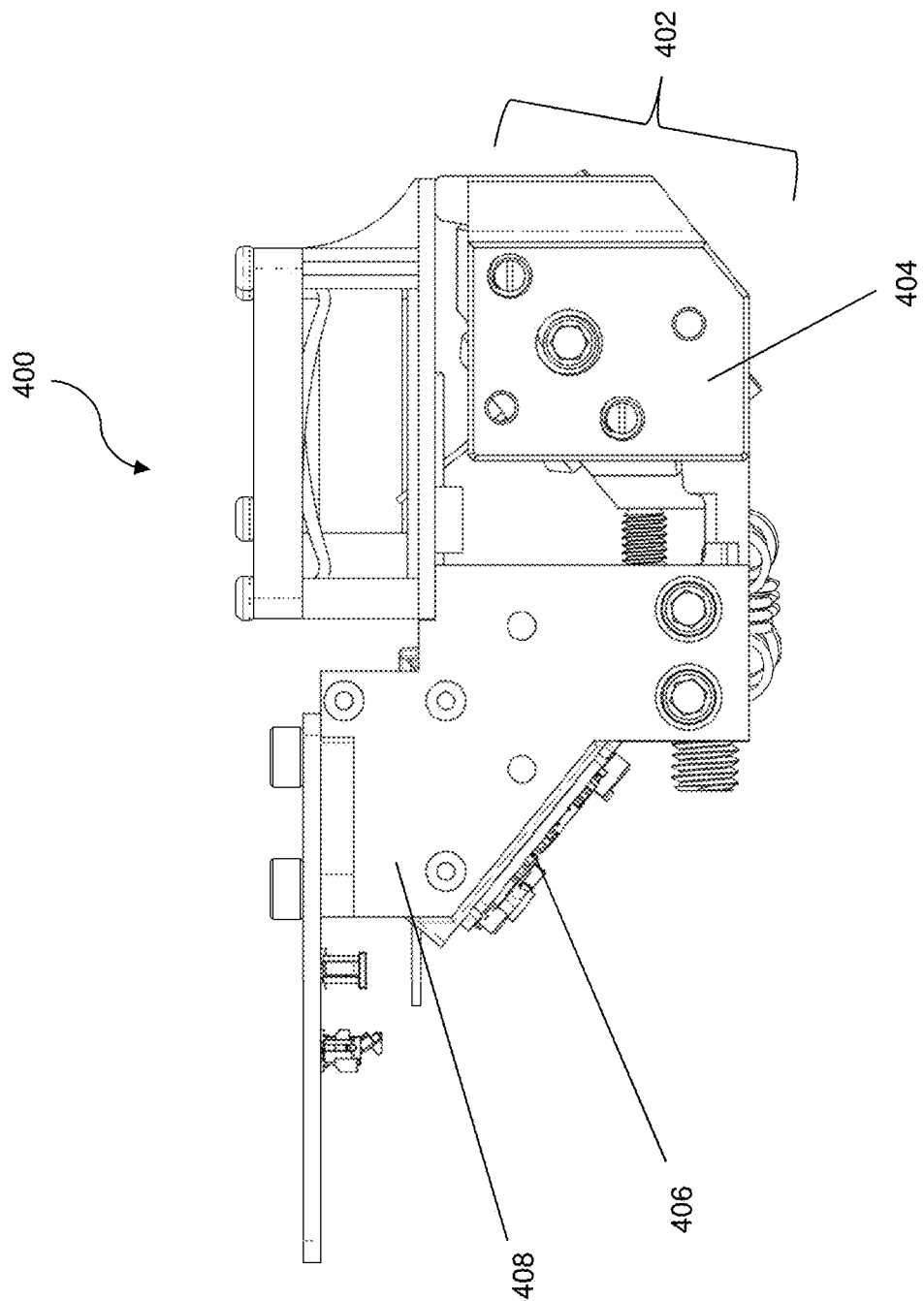
FIG. 4 illustrates a side view of one embodiment of an optical assembly typically found in the handheld interferometric system of FIG. 1.

FIG. 4 illustrates a side view of an exemplary embodiment of an optical assembly unit 400 that can be found in the handheld interferometric systems described herein (such as in FIGS. 1-2). The optical assembly unit 400 includes an light unit 402 aligned in an light unit housing 404. The optical assembly unit 400 includes a detector unit 406, such as a camera unit, aligned in a camera unit housing 408.

Figure 5A:
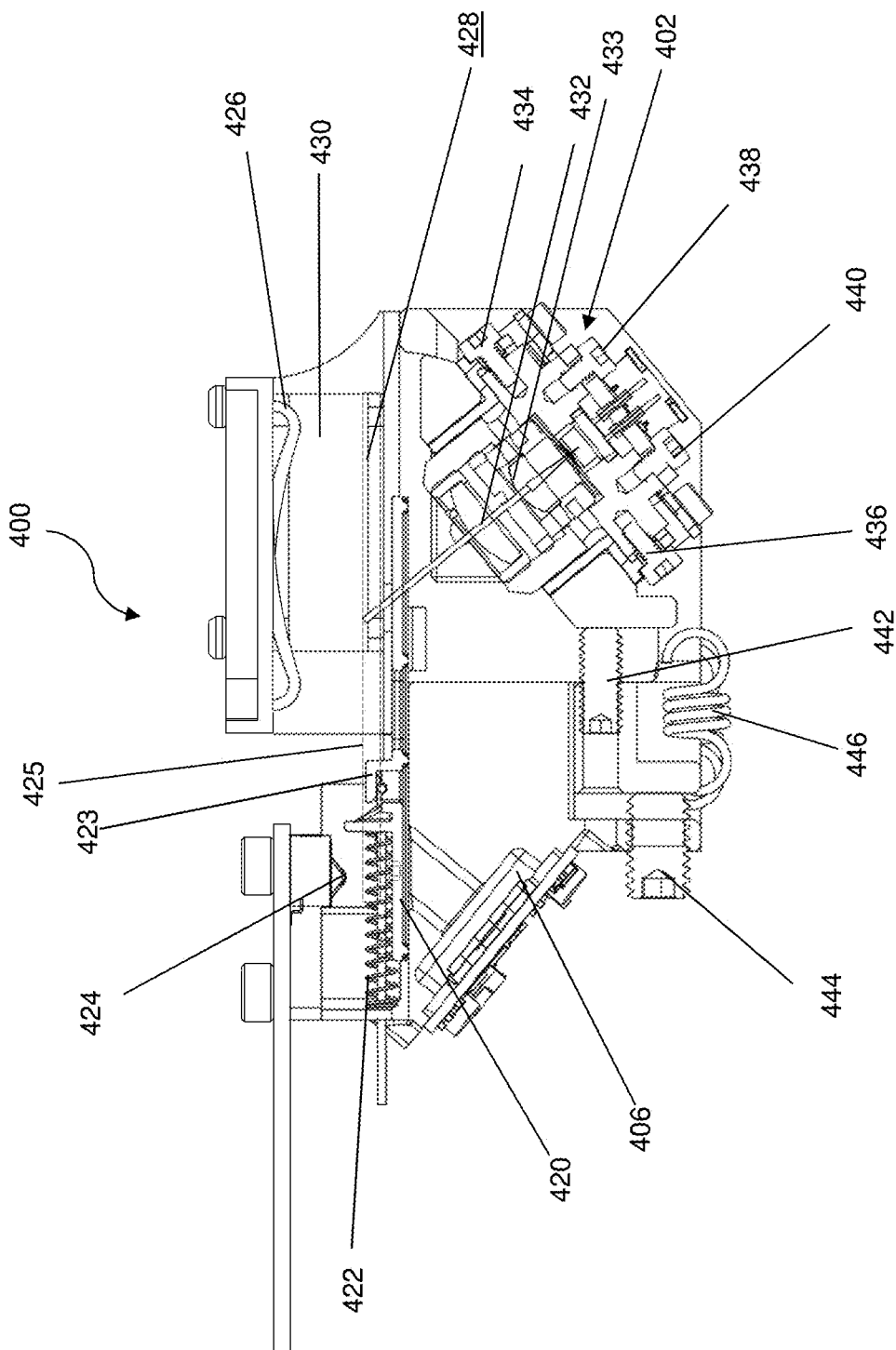
FIG. 5A illustrates a cross-sectional view of the optical assembly of FIG. 4.

FIG. 5A illustrates a cross-sectional view of the optical assembly unit 400 of FIG. 4. The light unit 402 is situated at an angle relative to the shutter flap element 420. The shutter flap element 420 is adapted to slide open and shut under tension from a shutter spring 422. The shutter flap element 420 is illustrated in a first, closed position with no cartridge system inserted. The shutter flap element 420 includes and upper control arm 423 that is located within a rail portion 425.

Figure 6:
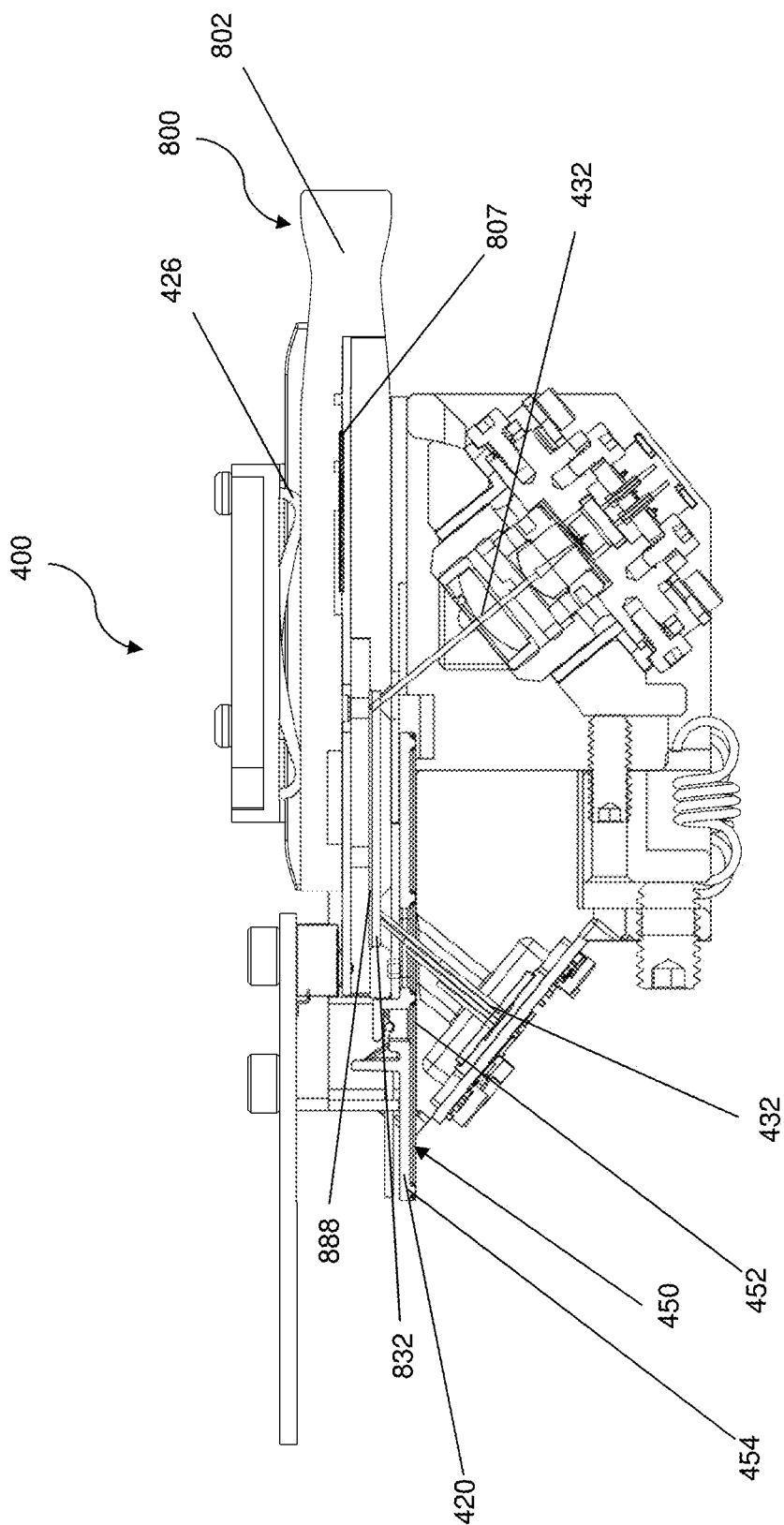
FIG. 6 illustrates the cross-sectional view of the optical assembly of FIG. 5A with one embodiment of a cartridge system inserted in the optical assembly.
Figure 8F:
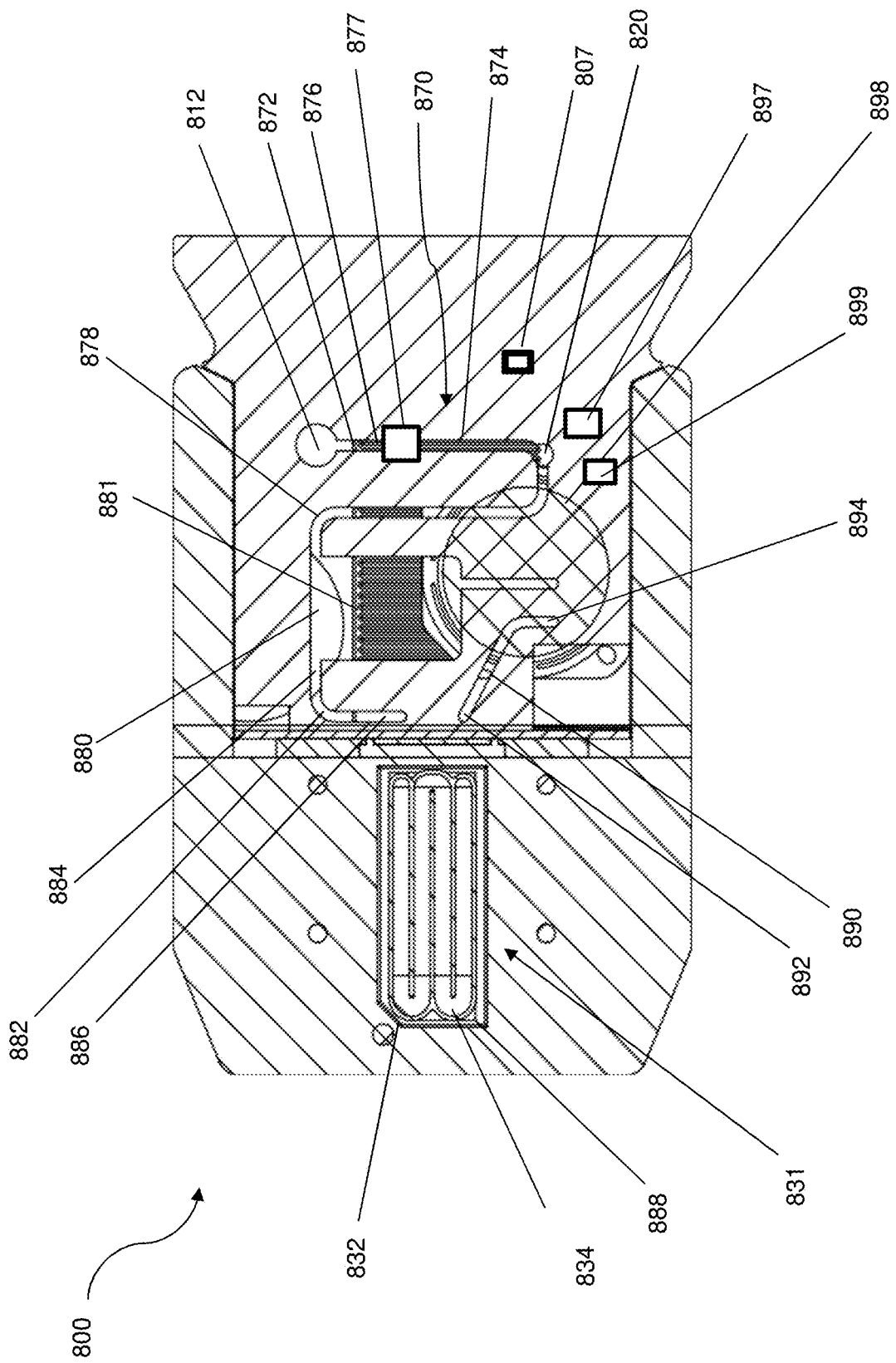
FIG. 8F illustrates a cross-section view (looking downward) of a single-use cartridge system along the horizontal line of FIG. 8E.
Figure 9B:
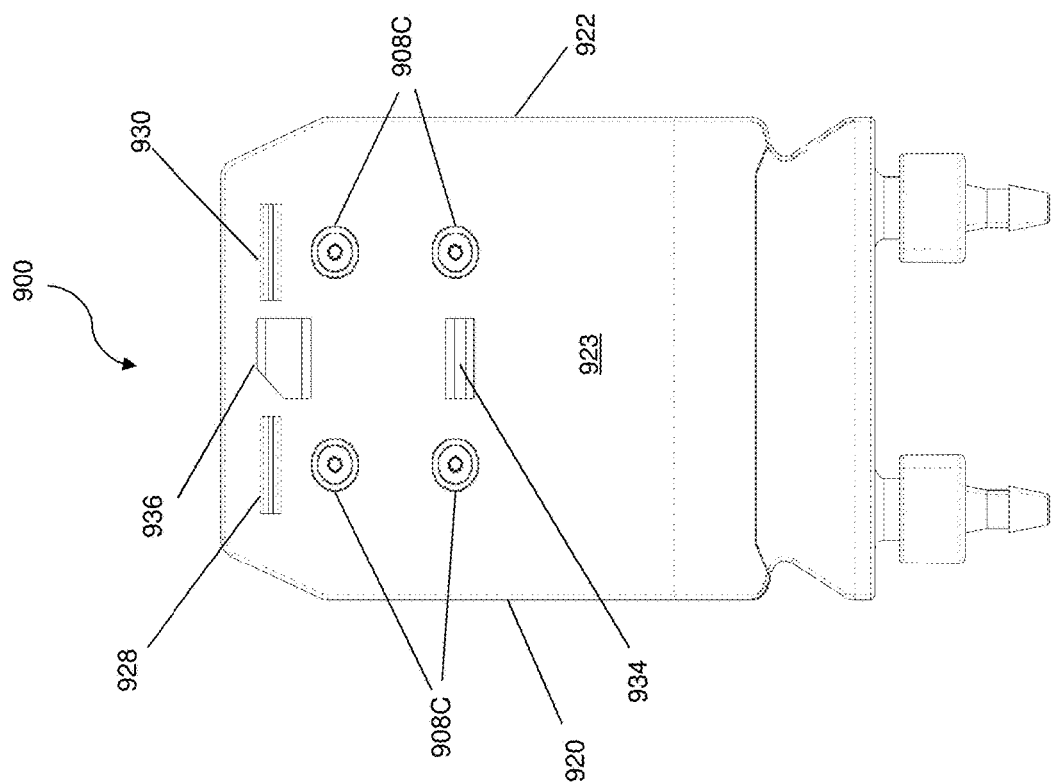
FIG. 9B illustrates a view of the bottom surface of one embodiment of a multi-use cartridge system.
Figure 9A:
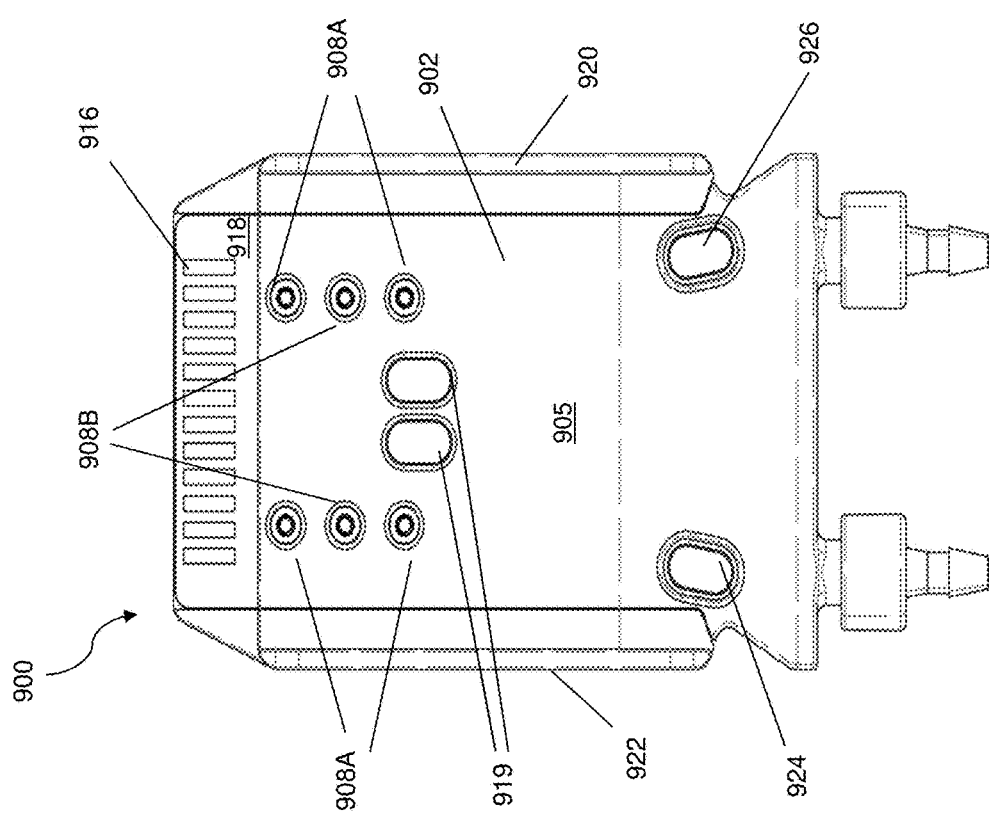
FIG. 9A illustrates a view of the top surface of one embodiment of a multi-use cartridge system.

A complimentary communication means 424 extends downward so as to make electronic contact with electronic communications means located on the cartridge housing (see FIGS. 6, 8A and 9A). The complimentary communication means 424 may be metal contacts such that, upon insertion, the metal contacts on the exterior surface of the cartridge housing touch and establish electronic communication between the cartridge system and the remaining components of the interferometric system (e.g., light unit, camera unit, etc.). The complimentary communication means 424, as illustrated, include one or more substantially pointed or "V" shaped so as to push down into or otherwise contact the cartridge housing metal contacts. The number of complimentary communication means 424 may match and align with the number of metal contacts on the exterior surface of the cartridge housing.

At least one downward cantilever bias spring 426 may be located within the optical assembly unit 400 such that, upon insertion of the cartridge through the interferometric system housing opening, the downward cantilever bias spring 426 pushes against a top side of the cartridge housing thereby forcing the cartridge housing against an opposite side or bottom portion or surface 428 of the cartridge recess 430 resulting in proper alignment along a vertical plane (see FIGS. 5A, 5B, 5C and 6).

The light unit 402 is optionally adjustable along various planes for optimal light signal 432 emission. As illustrated, the signal 432 is shown to be emitted and focused by at least one lens 433. A camera unit 406 is situated at an angle relative to the shutter flap element 420 so as to receive the light signal 432 upon exit from the cartridge (see FIG. 6).

A first roll adjustment screw 434 and second roll adjustment screw 436 are located on opposing sides of the light unit 402 for adjusting roll of the light unit 402. A first upward adjustment screw 438 and second upward adjustment screw 440 are located in a parallel manner on each side the light unit 402 for adjusting the light unit 402 towards the cartridge system (i.e., substantially upward). An angle of incidence screw 442 is located against the light unit 402 to allow for adjustments to the angle of incidence for proper coupling angle. A translation screw 444 is located direct communication with the light unit 402 to adjust translation in the X axis. A spring element 446 maintains the position of the light unit 402 against the light unit 402 by assisting the adjustment screws (432, 436), incidence screw 442 and translation screw 444.

Figure 5B:
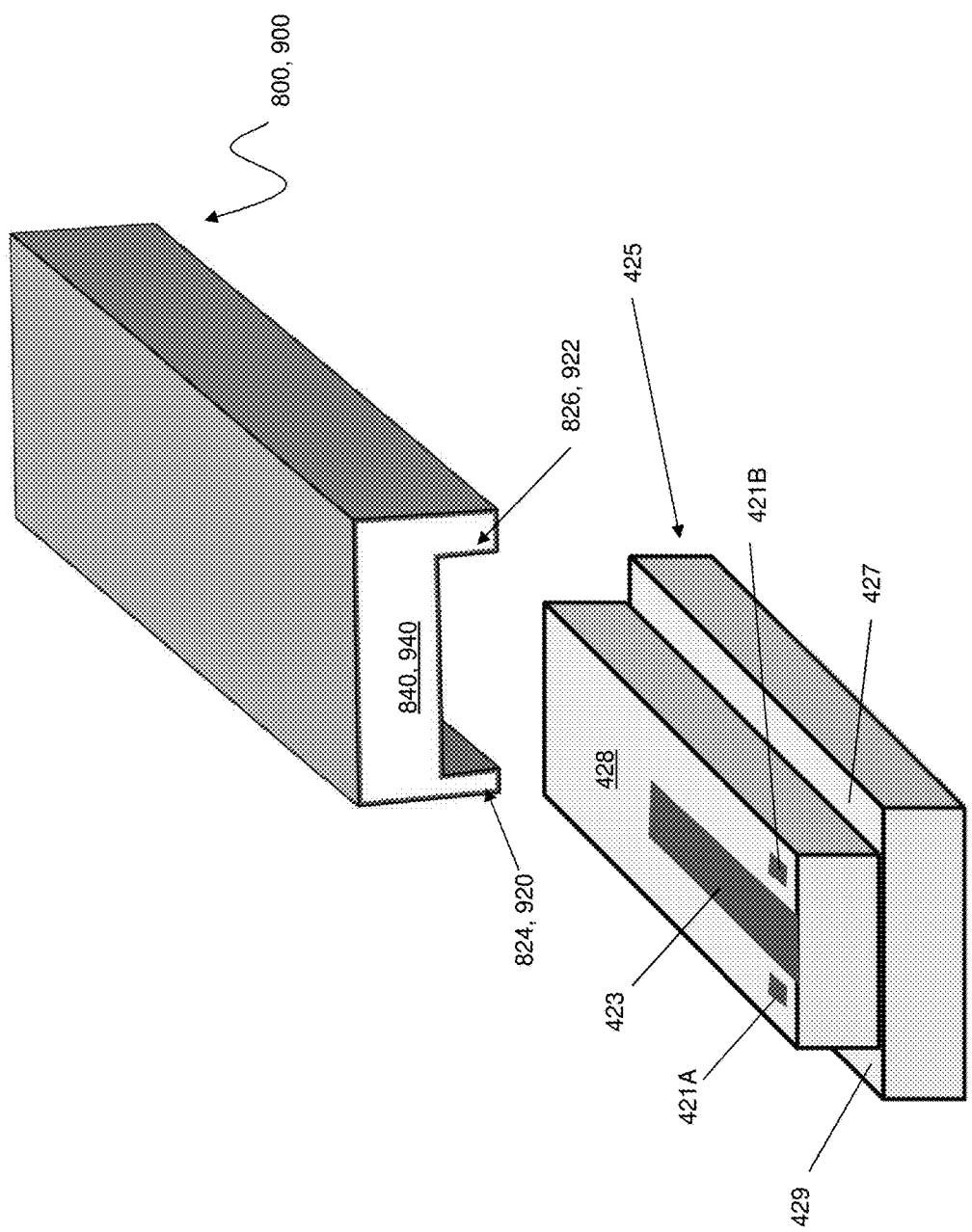
FIG. 5B illustrates an alignment means according to one embodiment.
Figure 5C:
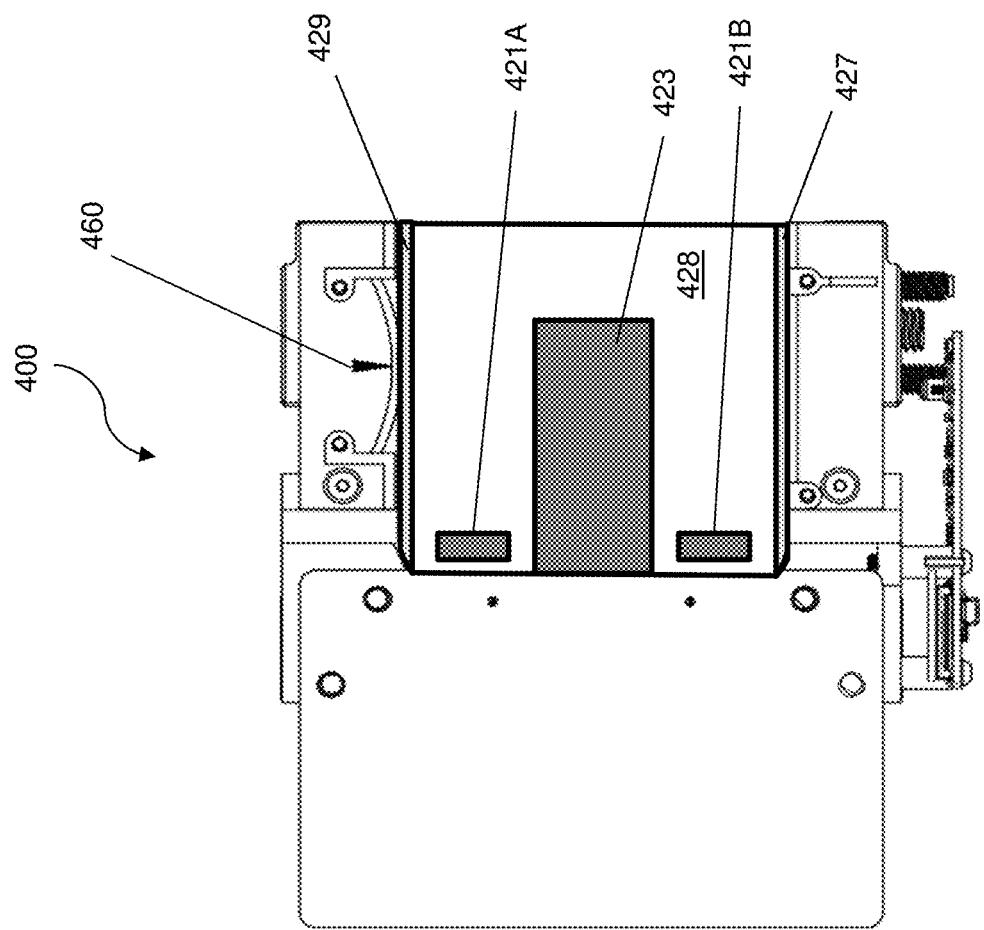
FIG. 5C illustrates an embodiment of a top view of the optical assembly and alignment means.

With specific regard to FIGS. 5A, 5B, and 5C, the bottom portion 428 of the cartridge recess 430 further includes alignment means that includes at least one rail portion 425 for engaging both male key portions on the cartridge housing (see 824, 826 of FIG. 8A; see 920, 922 of FIG. 9A). The bottom portion or surface 428 of the cartridge recess 430 includes a first raised surface 421A and second raised surface 421B. A shutter upper control arm 423 is located within the rail portion 425. The rail portion 425 includes a first rail wing 427 and second rail wing 429 adapted to receive and engage the male key portions (see 824, 826 of FIG. 8A; see 920, 922 of FIG. 9A). By including such alignment means, the cartridge systems provided here may only engage in a certain manner thereby preventing incorrect insertion and provided proper optical and microfluidic alignment.

FIG. 6 illustrates a cross-sectional view of the optical assembly 400 of FIG. 5A with one embodiment of a cartridge system 800 inserted in the optical assembly 400. As illustrated, the shutter flap element 420 is pushed backwards upon insertion of the cartridge system 800. While not shown, the shutter spring 422 is compressed backwards. The shutter flap element 420 moves along a track system 450 having a stationary male rail 452 on which a female rail portion 454 slides from a first, closed position with no cartridge system 800 inserted to a second, open position as illustrated in FIG. 6 upon cartridge system 800 insertion.

FIG. 6 further illustrates positioning of the cartridge system 800 in the optical assembly 400. The cartridge system 800 includes an interferometric chip 832 positioned below the flow cell wafer 888. The cartridge system 800 includes storage means 807 as provided herein positioned within the cartridge housing 802. While the cartridge system 800 is illustrated as a single-use system, the alignment and positioning of the single-use cartridge assembly may also apply to the multiple-use cartridge systems provided herein (e.g., see FIGS. 9A-9F).

FIG. 7 illustrates a top view of the optical assembly unit 400 of FIG. 5A with one embodiment of a cartridge system 800 inserted in the optical assembly unit 400. The cartridge system 800, as illustrated, is a single-use system, however, a multiple-use system may be inserted in the same manner within the interferometric system. The cartridge system 800 includes a cartridge housing 802 having a top surface 805. The optical assembly unit 400, as illustrated, includes a plurality of cantilever bias springs 426. The optical assembly unit 400 further includes at least one side bias spring 460 such that, upon insertion of the cartridge system 800, the side bias spring 460 pushes against one horizontal side 860 of the cartridge housing thereby forcing the cartridge housing 802 into proper alignment along a horizontal plane.

Cartridge System Overview

The cartridge systems provided herein includes a cartridge housing. The cartridge housing may be manufactured from any polymer suitable for single or multiple-use. The cartridge may be manufactured according to a variety of additive processing techniques such as 3-D printing. The cartridge may be manufactured via traditional techniques such as injection molding. The polymer may include a coefficient of expansion such that the housing does not expand or contract in a manner that would disrupt alignment of any microfluidic or detection components described herein when the cartridge is exposed to heat or cold environmental conditions.

The cartridge housing may include a light prevention means to aid in reducing, preventing or eliminating ambient, outside light from interfering the detection of one or more analytes. The light prevention means may include colored cartridge housing (e.g., black colored) that is color dyed or coated during manufacture. According to one embodiment, a dye may be introduced to the polymer to provide a specific color to a region of or the entire cartridge housing. Suitable colors include any color that aids in reducing, preventing or eliminating ambient, outside light from interfering the detection of one or more analytes.

The cartridge systems provided herein further includes a detection region. This detection region accommodates or is otherwise adapted to receive an interferometric chip and flow cell wafer. The flow cell wafer includes at least one detection microchannel. The flow cell wafer is located directly above the chip. The detection microchannel may be etched onto a flow cell wafer having a substantially transparent or clear panel or window. The flow cell wafer, the chip or both the flow cell and chip may be coated with a substance that reduces or eliminates fogging or condensation. According to one embodiment, the chip may be heated to reduce or elimination fogging or condensation.

The cartridge systems provided herein are configured or otherwise adapted or designed to easily insert and instantly align within an interferometric system such as, for example, a hand-held interferometric system. By being configured to allow for instant alignment, no further adjustment is required by a user to align any microfluidic components and any internal detection-related components such as the laser, chip with waveguides and exposed channels in a detection region of the cartridge, optical detector and any other focus-related components in the interferometric system.

The cartridge housing includes dimensions that are complimentary in size and shape to the size and shape to an internal surface defining a recess within an interferometric system. As provided and illustrated in the non-limiting examples herein, the cartridge housing may be generally rectangular in overall shape.

According to one embodiment, the cartridge system may be inserted and removed automatically. According to one embodiment, the cartridge housing contains a bar code or QR code. According to one embodiment, the cartridge system contains a bar code or QR code for calibration or alignment.

To aid in alignment, the cartridge housing includes an alignment means on an external surface of the cartridge housing. The alignment means many take a variety of forms that assure instant alignment of any microfluidic components and any internal detection-related components upon insertion of the cartridge within the interferometric system. The alignment means also aids in the prevention of incorrect orientation assertion within the interferometric system and allows for insertion only after proper alignment is attained. The alignment means further allows for the cartridge system to be stabilized to address vibrational distortions.

The alignment means may include at least one male key portion for engaging and securing within a corresponding female rail located in the interferometric system. The male key portion may be disposed on the bottom surface of the cartridge housing, however, the male key portion may be located on any exterior surface of the cartridge housing. Other suitable alignment means include one or more microswitches or sensing devices that guide the cartridge housing to assure proper alignment.

According to a particular embodiment, the cartridge housing includes a top portion and a bottom portion based on the orientation of insertion in an interferometric system. The top portion may include a top surface defining at least one through hole on at least one external surface of either the top portion or bottom portion. The at least one through hole is adapted to receive a removable fastening means for securing the top portion and bottom portion together. Suitable fastening means include screws or other suitable fastener that may be removed. By allowing the top portion and bottom portion of the cartridge housing to be separated and reattached, a user may open the cartridge housing to allow for cleaning as well as replacement of the chip.

The cartridge system as provided herein may include a temperature control means to control temperature as well as humidity. The cartridge system as provided herein may include a temperature control means to control test sample composition temperature. By controlling temperature and humidity around the cartridge system, the interferometric system can provide more repeatable, precise results. According to one embodiment, the cartridge system contains heating capability to facilitate consistent measurement and operation in cold temperatures. By controlling temperature and humidity around the cartridge system, fogging or condensation that causes interference in the detection region of the cartridge system is reduced or otherwise eliminated. The temperature control means may be located on or within the cartridge housing. According to a single-use cartridge system embodiment, the temperature control means is located on or around the mixing bladder of the microfluidic fluid system described herein. The temperature control means may be located on an exterior surface of the cartridge housing. One suitable temperature control means includes a metal coil that is heated upon introduction of an electric current. Another suitable temperature control means includes one or more warming bands or Peltier devices that can provide heating or cooling.

Each of the cartridge systems described herein include a flow cell having at least one detection microchannel adapted to communicate with one or more test sample compositions flowing through a chip beneath the flow cell. According to one embodiment, the cartridge systems may include at least two detection microchannels with each detection microchannel adapted to communicate one or more test sample composition allowing detection of the same or different analytes. According to one embodiment, cartridge system includes a flow cell having at least three detection microchannels with each detection microchannel adapted to communicate one or more test sample composition allowing detection of the same or different analytes. According to one embodiment, cartridge system includes a flow cell having at least four detection microchannels with each detection microchannel adapted to communicate one or more test sample composition allowing detection of the same or different analytes.

Cartridge System—Exemplary Embodiments

An exemplary embodiment of a single-use cartridge system 800 is illustrated in FIGS. 8A-F. A top view of a cartridge system 800 is provided in FIG. 8A. The cartridge system 800 includes a cartridge housing 802 as described herein. The housing 802 includes a top portion 804 (see FIG. 8C) having a top surface 805. The top surface 805 includes four heat stake posts 808 for joining the top portion 804 of the cartridge housing 802 to a bottom portion 810 (See FIG. 8C) of the cartridge housing 802. By utilizing heat stake posts 808, the top portion 804 may be permanently joined to a bottom portion 810 of the cartridge housing 802. The top surface 805 includes an injection port 812 for introduction of a test sample.

The cartridge housing 802 further includes an electronic communication means 816 located on a second external surface 818 that is on a different horizontal plane from the top surface 805. The electronic communication means 816 as illustrated includes a plurality of metal contacts.

The cartridge system further includes a vent port 820. The vent port 820 allows for any air in the microfluidic system 870 (see FIG. 8F), such as in the form of bubbles, to exit. The vent port 820 may include a vent cover 821 over the vent port 820. The vent cover 821 may be fabricated from a material that repels liquid while allowing air or vapor to pass through such as, for example, expanded polytetrafluoroethylene (commercially available as Goretex®. The vent cover 821 allows for air purging from the cartridge system 800 but will not allow fluid to pass through such as when a vacuum is applied to prime the microfluidic system 870. In this way, bubble formation in a liquid test sample composition is removed or otherwise avoided. The top surface 805 also includes two port seals 822. The port seals 822 may be made from rubber and provides sealing of the microfluidic system 870 within the cartridge system 800.

FIG. 8B illustrates a view of the bottom surface 823 of one embodiment of a single-use cartridge system 800. The bottom surface 823 includes a first male key portion 824 and a second male key portion 826. The male keying portions (824, 826) engage with a corresponding rail portion (425—See FIGS. 5A, 5B and 5C) located in the cartridge recess 430 of the optical assembly 400. The bottom surface 823 further defines a first detent 828 and a second detent 830. The detents (828, 830) engage with or otherwise receive a corresponding first raised surface and a second raised surface (421A, 421B) inside the cartridge recess 430 of the optical assembly 400 (see FIGS. 5A, 5B and 5C). When engaged with the first detent 828 and second detent 830, the first raised surface and second raised surface (421A, 421B) aid in securing the cartridge system 800 within the cartridge recess 430.

The chip 832 is substantially transparent and allows the light signal to enter, interact with one or more waveguides channels (See FIG. 3C) and allow for binding of analyte flowing within the at least one detection microchannel 834 within the flow cell wafer 888.

The bottom surface 823 further defines a light inlet slot 836. The light inlet slot 836 allows for an light signal to enter the cartridge system 800. Particularly, the light inlet slot 836 allows for an light signal to enter the chip 832 and for the light signal to move through any waveguide channels (not shown; see e.g., part 316 of FIG. 3C) in the chip 832 while interacting with analytes in the at least one detection microchannel 834 before the light signal is deflected by one or more gratings (not shown) down to the detector unit 406 (see e.g., FIGS. 3C and 6).

FIG. 8C illustrates a view of the back surface 840 of the cartridge housing 802 of a single-use cartridge system 800. The cartridge housing 802 includes a top portion 804 and a bottom portion 810. The male keying portions (824, 826) are shown extending from the bottom portion 810 of the cartridge housing 802.

FIG. 8D illustrates a view of the front surface 850 of the cartridge housing 802 of a single-use cartridge system 800. The male keying portions (824, 826) are shown extending from the bottom portion 810 of the cartridge housing 802.

FIG. 8E illustrates a view of one side surface 860 of the cartridge housing 802 of a single-use cartridge system 800, the opposing side being a mirror image.

FIG. 8F illustrates a cross-section view downward of a single-use cartridge system 800 along the horizontal line of FIG. 8E. The cartridge system 800 includes a detection region 831 that accommodates or is otherwise adapted to receive a chip 832 and flow cell wafer 888. The single-use cartridge system 800 includes a microfluidic system 870 for communicating or otherwise providing a means for a test sample composition to move through the cartridge system 800 and allow for detection and analysis of one or more analytes. The microfluidic system 870 includes an injection port 812 for introduction of a test sample. The injection port may 812 optionally include a check valve 872. The microfluidic system 870 further includes a first microchannel section 874 having a first end 876 attached in communication with the injection port check valve 872 and a second end 878 in communication with a mixing bladder 880. A filter 877 may be located anywhere within the first microchannel section 874. The microfluidic system 870 also includes a vent port 820 within the first microchannel section 874 between the first end 876 and second end 878. The mixing bladder 880 includes a temperature control means 881 in the form of a metal coil wrapped around the mixing bladder 880 such that the temperature control means 881 is heated upon introduction of an electric current.

The microfluidic system 870 further includes second microchannel section 882 having a first end 884 attached in communication with the mixing bladder 880 and a second end 886 attached in communication with a flow cell wafer 888 having at least one detection microchannel 834.

The microfluidic system 870 further includes third microchannel section 890 having a first end 892 attached in communication with at least one detection microchannel 834 and a second end 894 in communication back to the mixing bladder 880 so as to form a closed loop.

The microfluidic system 870 further includes at least one micropump 898. The micropump 898, as illustrated, is a piezoelectric pump that overlays or otherwise engages or touches one or more of the first microchannel section 874, second microchannel section 882, third microchannel section 890 and mixing bladder 880. The micropump 898 manipulates the communication of test sample composition throughout the microfluidic system 870.

The single-use cartridge system 800 may further include a transmission component 897 as provided herein. The single-use cartridge system 800 may further include a location means 899 as provided herein.

An exemplary embodiment of a multiple-use cartridge system 900 is illustrated in FIGS. 9A-F.

A top view of an embodiment of a multi-use cartridge system 900 is provided in FIG. 9A. The cartridge system 900 includes a cartridge housing 902 as described herein. The housing 902 includes a top portion 904 (see FIG. 9C) having a top surface 905. As illustrated, the top surface 905 includes four top through holes 908A. The top through holes 908A are adapted (e.g., threaded) to receive a removable fastening means (not shown) for securing the top portion 904 to a bottom portion 910 (see FIG. 9C). The top surface also includes two sealing holes 908B that allow for sealing of the chip 936 to the cartridge housing 902.

The cartridge housing 902 further includes an electronic communication means 916 located on a second external surface 918 that is on a different horizontal plane from the top surface 905. The electronic communication means 916 as illustrated includes a plurality of metal contacts. The top surface 905 also includes two port seals 919 and two seal plugs (924, 926).

FIG. 9B illustrates a view of the bottom surface 923 of a multiple-use cartridge system 900. The bottom surface 923 includes a first male key portion 920 and a second male key portion 922. The male keying portions (920, 922) engage with a corresponding rail portion (425—See FIGS. 5A, 5B and 5C) located in the interferometric system. The bottom surface 923 further defines a first detent 928 and a second detent 930. The detents (928, 930) engage with or otherwise receive a corresponding first raised surface and a second raised surface (421A, 421B) inside the cartridge recess 430 of the optical assembly 400 (see FIGS. 5A, 5B and 5C). When engaged with the first detent 928 and second detent 930, the first raised surface and second raised surface (421A, 421B) aid in securing the cartridge system 900 within the cartridge recess 430.

The bottom surface further includes bottom through holes 908C that align and correspond to the four top through holes 908A. The bottom through holes 908C may be adapted (e.g., threaded) to receive a removable fastening means (not shown) for securing the top portion 904 to a bottom portion 910 (see FIG. 9C).

The bottom surface 923 further defines a light inlet slot 934. The light inlet slot 934 allows for an light signal to enter the cartridge system 900. Particularly, the light inlet slot 934 allows for an light signal to enter the chip 936 and for the light signal to move through any waveguides in the chip 936 while interacting with analytes in the at least one detection microchannel 994 (see FIG. 9F) before the light signal is deflected by one or more gratings (not shown) down to the detector unit 406 (see FIG. 6).

FIG. 9C illustrates a view of the back surface 940 of one embodiment of a multiple-use cartridge system 900. The housing includes a top portion 904 that is optionally removable from a bottom portion 910. The male keying portions (920, 922) are shown extending from the bottom portion 910 of the cartridge housing 902.

FIG. 9D illustrates a view of the front surface 950 of one embodiment of a multiple-use cartridge system 900. FIG. 9E illustrates view of one side surface 960 of one embodiment of a single-use cartridge system 900, the opposite side being a mirror image.

Figure 9F:
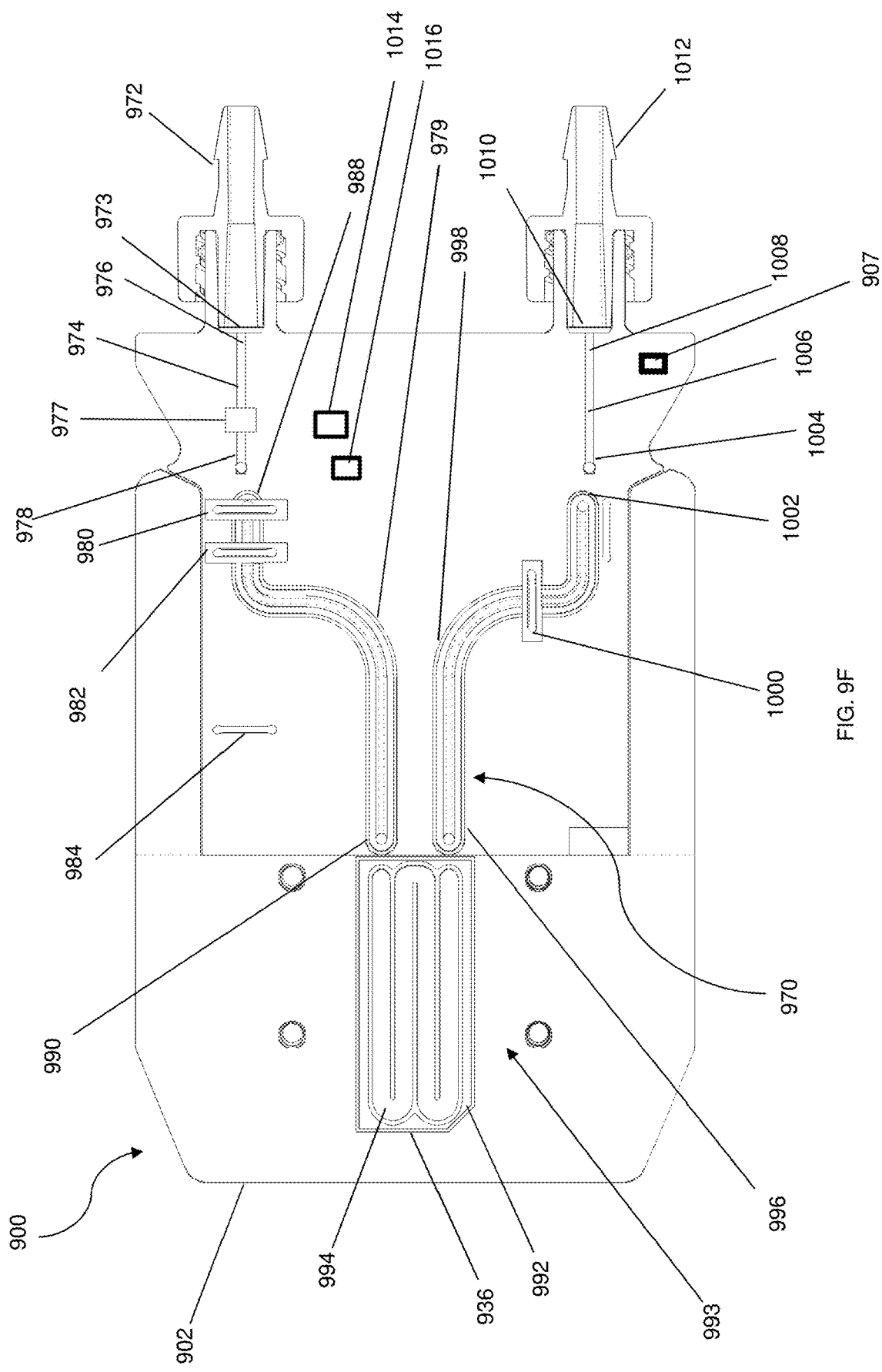
FIG. 9F illustrates a cross-section view (looking downward) of one embodiment of a multi-use cartridge system along the horizontal line of FIG. 9E.

FIG. 9F illustrates a cross-section view downward of a multiple-use cartridge system 900 along the horizontal line of FIG. 9E. The cartridge system 900 a storage means 907 as provided herein positioned within the cartridge housing 902. The multiple-use cartridge system 900 includes a microfluidic system 970 for communicating or otherwise providing a means for a test sample composition to move through the cartridge system 900 and allow for detection and analysis of one or more analytes. An ingress port 972 is located on a front surface 950 (see FIG. 9D) of the multiple-use cartridge system 900. The ingress port 972 is in communication with a first microchannel section 974 having a first end 976 attached in communication with an ingress port check valve 973 and a second end 978 in communication with second microchannel section 979. A filter 977 may be located anywhere within the first microchannel section 974. A sample electrode 980 and reference electrode 982 are in contact with the second microchannel section 979. Impedance may be measured between the sample electrode 980 and reference electrode 982 to confirm the presence of test sample composition.

A valve test structure connection 984 is in communication with any test sample composition in the microfluidic system 970. The valve test structure connection 984 may be fabricated from nitinol shape memory alloy and aids in the movement of test sample composition into the cartridge system 900.

The second microchannel section 979 includes a first end 988 in communication the first microchannel section 974 and a second end 990 in communication with a flow cell 992 having at least one detection microchannel 994. The cartridge system 900 includes a detection region 993 that accommodates or is otherwise adapted to receive the chip 936 and flow cell 992. The chip 936 is substantially transparent and allows the light signal to enter, interact with one or more waveguides channels (not shown; see e.g., part 316 of FIG. 3C) and allow for binding of analyte flowing within the at least one detection microchannel 994 within the flow cell 992.

The detection microchannel 994 is in communication with a first end 996 of a third microchannel section 998. The third microchannel section 998 includes a flow electrode 1000 to approximate flow rate and is correlated with measured impedance. The third microchannel section 998 includes a second end 1002 in communication with the first end 1004 of a fourth microchannel 1006. The fourth microchannel 1006 includes a second end 1008 in communication with a check valve 1010 which, in turn, is in communication with an egress port 1012. The sample electrode 980, reference electrode 982, and flow electrode 1000 are each fabricated from inert nitinol or other corrosion-resistant conductive material.

The multiple-use cartridge system 900 may further include a transmission component 1014 as provided herein. The multiple-use cartridge system 900 may further include a location means 1016 as provided herein.

Figure 10:
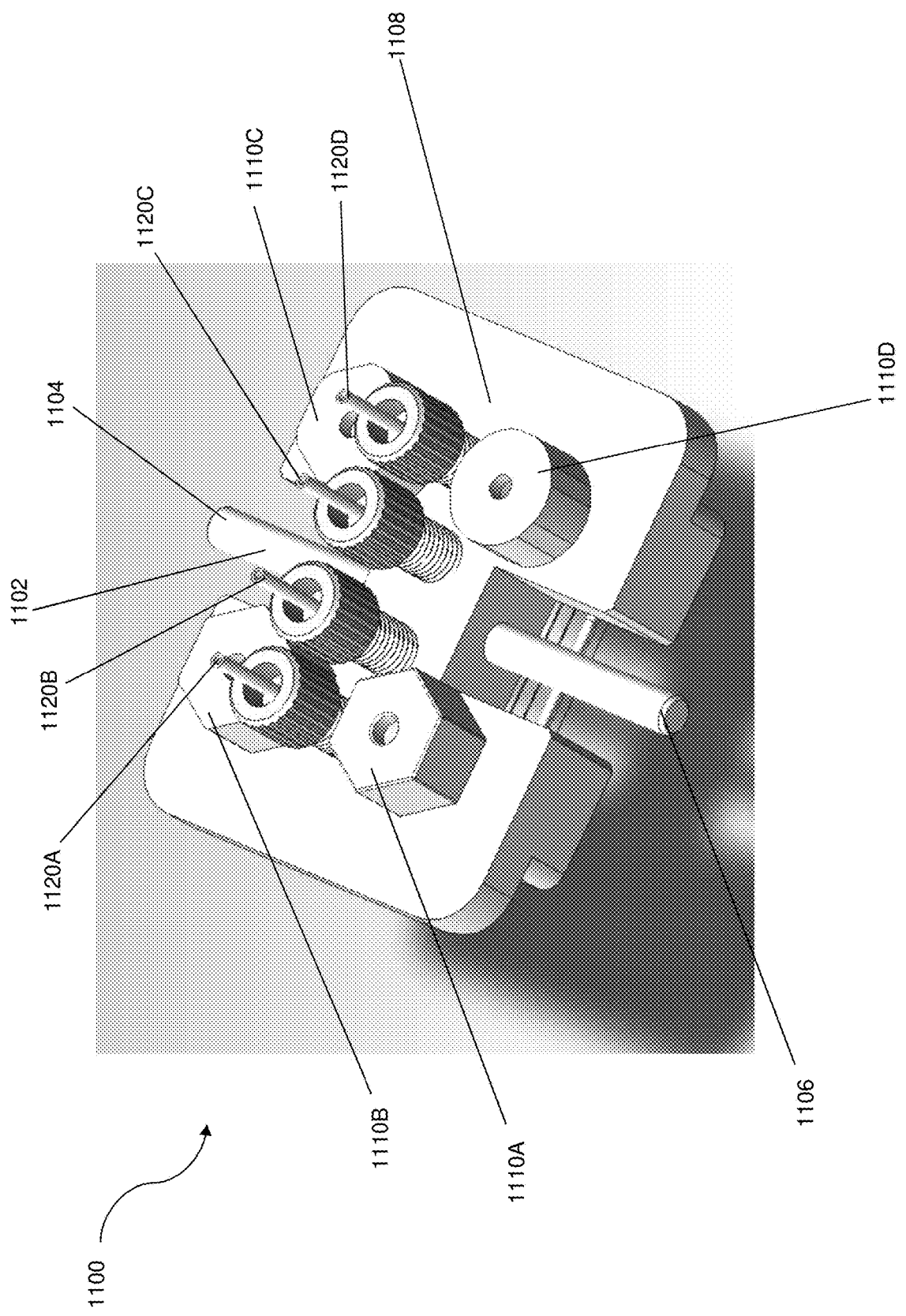
FIG. 10 illustrates a perspective view of an alternative single-use cartridge system.

An exemplary embodiment of an alternative single-use cartridge system 1100 is illustrated in FIG. 10. According to the illustrated embodiment, the cartridge system 1100 includes a connection mechanism 1102 (or snap-in rod) having opposing ends (1104, 1106) extending from the housing 1108. The connection mechanism 1102 aids in securing and interfacing the cartridge system 1100 with an interferometric system. Rising from the housing 1108, are an injection ports 1110 A-D and outlet ports 1120 A-D. The injection ports 1110 A-D may be utilized for introducing a test sample, buffer or a test sample composition. The cartridge system includes four independent detection microchannel ports that are independently in communication with a corresponding detection microchannel (not shown) within a flow cell (not shown). Buffer may be pre-loaded in the flow cell. Any test sample composition waste may be collected from the outlet ports 1120 A-D.

Aquatic Applications

By being mobile and utilized near the aquatic environment in question, a user may receive results in an efficient manner and any care or remedial measure decisions may be implemented immediately. The interferometric systems provided herein provide a major technical advancement in the fight to diagnose and track pathogens that are the cause of rising, recurring or endemic diseases as well as invading species of pathogen in an aquatic environment. The systems provided herein provide a means to indicate and otherwise aid in the control of disease surveillance, invasive species of pathogen and pandemic or widespread outbreak control. The systems provided herein also provide a means to assess water quality as well as serve as a microbe-based monitoring system to provide an early warning system for detection of unwanted pathogens in an aquatic environment.

According to a particular embodiment, the systems provided herein may be utilized to detect and quantify levels of pesticide in an aquatic environment. By providing detection and quantification data in an efficient manner within the aquatic environment, application and control rate of pesticide may be monitored, adjusted and otherwise controlled. According to such an embodiment, the system will detect and quantify pesticide at the parts per million (ppm) level. According to another embodiment, the system will detect and quantify pesticide at the parts per billion (ppb) level. According to another embodiment, the system will detect and quantify pesticide at the parts per trillion (ppt) level.

According to a particular embodiment, the systems provided herein may be utilized to detect and quantify levels of an aquatic herbicide (e.g., 2,4-D (2,4-dichlorophenoxyacetic acid) and flumioxazin (2-[7-fluoro-3,4-dihydro-3-oxo-4-(2-propynyl)-2H-1,4-benzoxazin-6-yl]-4,5,6,7-tetrahydro-1H-isoindole-1,3(2H)-dione)) in an aquatic environment. By providing detection and quantification data in an efficient manner within the aquatic environment, application and control rate of herbicide may be monitored, adjusted and otherwise controlled. Such control increases the efficiency of aquatic vegetation management. Such vegetation may include water hemp, duck weed or algae.

According to one embodiment, the system may be utilized to detect and quantify analytes from any vessel or container that may come internally in contact with an analyte such as a chemical contaminant. The system as provided herein may be placed in fluid communication with a vessel so as to detect and quantify analytes in real time. Fluid communication may be established via a tube or other conduit that allows any fluid containing the fluid containing the aquatic test sample composition to come in contact with, or flow through, the system as provided herein.

According to one particular embodiment, the interferometric system provided here may be utilized in connection with or otherwise equipped to a mobile vehicle. Suitable mobile vehicles include, but are not limited to, unmanned aerial vehicles (UAV), unmanned ground vehicles (UGV), drones, manned aircraft, and manned vehicles.

Methods of Detection and Quantification

Figure 11:
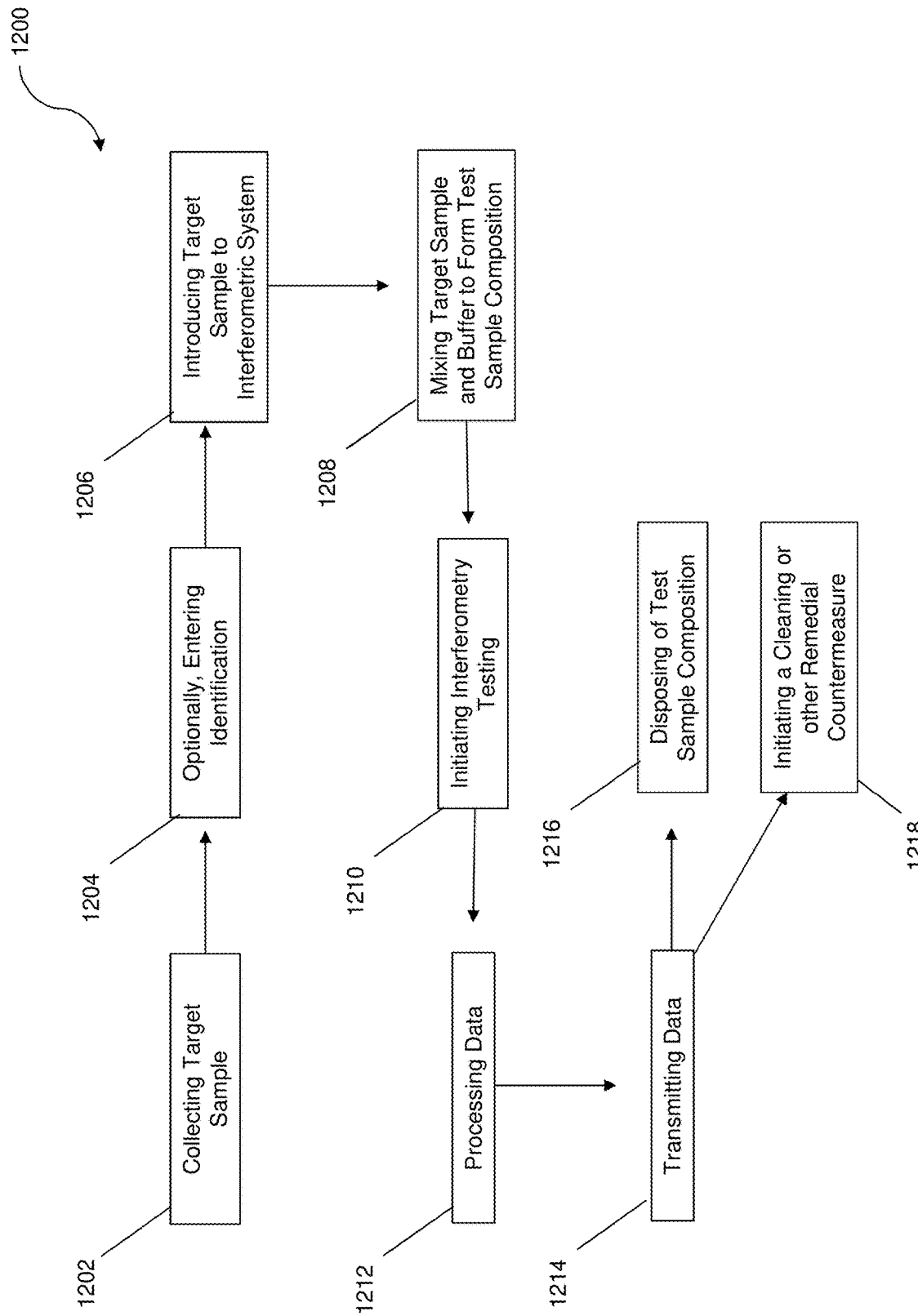
FIG. 11 illustrates a method of detecting and quantifying the level of analyte in an aquatic test sample composition.

FIG. 11 illustrates a method 1200 of detecting and quantifying the level of analyte in an aquatic test sample composition. The method includes the step of collecting 1202 or otherwise obtaining a target sample having one or more analytes. In different embodiments, the target sample may be taken from the appropriate target depending on the location and environment.

According to one embodiment, the method further includes the optional step of entering 1204 a user identifier (ID) in the system. Additionally, an identification number associated with the sample, analyte or interest or a combination thereof may be entered. The cartridge system utilized may be equipped with a label or sticker carrying identifying such information. The label or sticker may include a QR code including such information. The label or sticker may be removed prior to use. Identifying information may include metadata such as time, GPS data, or other data generated by the interferometric system.

According to one embodiment, the method further includes the step of introducing the target sample to the interferometric system 1206. According to one embodiment, target sample is introduced to the cartridge by a separate device such as a syringe or pump. According to one embodiment, target sample is introduced by an injection device. According to one embodiment, the injection device may be permanently attached to the cartridge system. According to one embodiment, the injection device is a pipette. According to one embodiment, the injection device is a syringe. According to one embodiment, the injection device is a lance, pipette or capillary tube. When utilizing a multiple-use cartridge system, the cartridge system may be fitted to a tube or other transfer mechanism to allow the sample to be continuously taken from a large amount of fluid that is being monitored.

According to one embodiment, the method further includes the step of mixing 1208 the target sample with a buffer solution to form a test sample composition. In a multiple-use cartridge system, such a step may occur prior to the test sample composition being introduced to the cartridge system. In a single-use cartridge system, such a step may occur in the mixing bladder with the assistance of a pump.

The method of detecting and quantifying the level of analyte in a sample includes initiating waveguide interferometry 1210 on the test sample composition. Such a step may include initiating movement of the light signal through the cartridge system as provided herein and receiving the light signal within the detector unit. Any changes in an interference pattern are representative of analyte in the test sample composition. Particularly, such changes in an interference pattern generate data related to one or more analyte in the test sample composition. According to one embodiment, the step of initiating 1210 waveguide interferometry on the test sample composition includes the step of correlating data from the phase shift with calibration data to obtain data related to analyte identity, analyte concentration, or a combination thereof.

According to one embodiment, the method further includes the step of processing 1212 any data resulting from changes in the interference pattern. Such changes in interference pattern may be processed and otherwise translated to indicate the presence and amount of an analyte in a test sample composition. Processing may be assisted by software, processing units, processor, servers, or other component suitable for processing. The step of processing data may further include storing such data in storage means as provided herein.

According to one embodiment, the method further includes the step of transmitting a data signal 1214. The signal may result in the display of data on the system. The step of transmitting data may include displaying the analyte levels via projecting any real time data on a screen as described herein. The step of transmitting data may include transmitting any obtained data to a mobile phone, smart phone, tablet, computer, laptop, watch or other wireless device. The data may also be sent to a device at a remote destination. The remote destination device may be a locally operated mobile or portable device, such as a smart phone, tablet device, pad, or laptop computer. The destination may also be smart phone, pad, computer, cloud device, or server. In other embodiments, the remote destination may be a stand-alone or networked computer, cloud device, or server accessible via a local portable device. A diagnosis of an infection in an aquatic environment may be based on the analyte quantity. The diagnosis may be based on the use of one or more immunoglobulins as detection materials.

The method may optionally include the step of disposing of the test sample composition 1216 per legal requirements. Such legal requirements assure that any sample still containing unacceptable levels of pathological contamination are disposed of properly so as not to cause harm to a user or the environment.

According to one embodiment, the method further includes the step of initiating 1218 a cleaning or remedial countermeasure against any analyte detected. Such remedial measure may include introducing cleaning chemicals or beneficial microorganisms to the aquatic environment. The remedial measures may work to kill or otherwise neutralize any unwanted analyte present in the aquatic environment where a sample was taken.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be apparent to those skilled in the art, and all modifications that do not depart from the spirit of the disclosure are intended to be included with the scope of the appended claims.

PROPHETIC EXAMPLE 1

Cholera and Cyanobacteria Detection and Quantification

A point of use testing unit may be set up to aid in rapid detection and quantification of cyanobacteria, cholera (*Vibrio cholera*), or a combination thereof in a surface water source. Cholera and cyanobacteria are known to maintain a symbiotic relationship so there may be a need to test for both analytes.

A user may obtain a sample from the water source. A cartridge is then placed inside the system's detector component, if not already present. The cartridge may be fully replaceable and disposable after each use. The user may optionally then enter a user identifier (ID) in the system and the system optionally transmits that information to the remote server for authentication or stores the information locally. Any of a number of identifier labelling techniques, such as radio frequency identifiers (RFIDs) on or within a sample may be used. Alternatively, a unique serial number, code or other identifier associated with a sample may be manually entered into the system and optionally transmitted to a remote server. Additionally, the user may use the system to scan in or manually enter one or more substance/contaminant identifiers, such as a Universal Product Code (UPC) for the one or more analytes believed to be present in the sample and to inform the remote server of the one or more analytes. The system may also include geolocation information in its communications with the server, either from a GPS sensor included in the system or a GPS software function capable of generating the location of the system in cooperation with a cellular or other communication network in communication with the system.

For detection and quantification of a cyanobacteria, one or more antibodies specific to the cyanobacteria will be included on the receptor layer. The antibodies may be specific to microcystins such as microcystin-LR that are found in connection with cyanobacteria.

If present, the user may initialize the system by pressing a start button or other similar means to initiate any electronic components present in the system. If present, the user may optionally press an injection bulb or similar mechanical component to inject a buffer solution into the cartridge. Any display on the system may then provide visual signal that the system is ready for sample introduction (e.g., signal "READY"). If present, the user may then press another external display or button to signal the system that a sample is ready to be introduced (e.g., "SAMPLE").

To introduce a sample, an aliquot of the sample may be added through a sample collecting component. Such a step may be accomplished via a disposable pipette or similar device that is suited for storing a sample until needed. Next, a user may press the injection bulb or similar mechanical component to mix the aliquot of sample and buffer and introduce the mixture to the cartridge. According to an alternative embodiment, the buffer may be mixed with the aliquot sample in a separate step prior to introduction to the cartridge. A user may then press the injection bulb or similar mechanical component a one or more times to ensure the sample mixture has fully transitioned or otherwise migrated to the cartridge and begins flowing across the waveguide channels on the waveguide. Upon arrival at the waveguide, detection and quantification processes are undertaken. Depending on the goal of the point of use procedure, one or more analytes in the sample will bind to the receptor surface of the waveguide channels thereby altering the evanescent field above the waveguide channels. The changes in the interference pattern will then create an electronic signal that can be translated to produce a reading on a display on an external surface of the system. Any collection devices and used interferometric cartridges used during use may then be disposed of properly in an appropriate waste container. The cartridge within the system may then be removed and replaced with a new cartridge or cleaned prior to next use. The cartridge may be fully disposable and placed in an appropriate waste container.

PROPHETIC EXAMPLE 2

Ground Water Analyte Detection

A point of use testing unit may be set up to aid in rapid detection and quantification of one or more target analytes in a subterranean water source (e.g., ground water). A duser may obtain a sample from the water source and carry out the steps as set forth with respect to Example 1. The targeted analytes may include any chemical contaminant including, but not limited to, a volatile organic compound such as benzene, toluene, ethylbenzene and xylenes), tetrachloroethylene (PCE), trichloroethylene (TCE), vinyl chloride (VC), and gasoline. Other chemical contaminants include oil, nitrites, metals, and pesticides.

We claim:

1. A portable interferometric system for detection and quantification of analyte within an aquatic test sample composition, the system comprising:
    an optical assembly unit, the optical assembly unit comprising a light unit and a detector unit each adapted to fit within a portable housing unit; and
    a cartridge system adapted to be inserted in the housing unit and removed after one or more uses, the cartridge system comprising:
        an interferometric chip including one or more waveguide channels having a sensing layer thereon, the sensing layer adapted to selectively bind or otherwise be selectively disturbed by one or more analytes within the aquatic test sample composition; and
        a flow cell wafer; and
        a cartridge housing enclosing the interferometric chip and flow cell wafer; and
    an alignment means for aligning the cartridge system within a cartridge recess in the optical assembly unit upon insertion thereby providing optical and microfluidic alignment of the interferometric chip and flow cell wafer.

2. The portable interferometric system of claim 1, wherein the portable housing is sized and shaped to fit in a user's hand.

3. The portable interferometric system of claim 1, further comprising at least one display unit.

4. The portable interferometric system of claim 1, further comprising an external camera, the external camera adapted to capture a photo or video.

5. The portable interferometric system of claim 1, the alignment means comprising at least one male key portion on an exterior surface of the cartridge housing for engaging and securing the cartridge within a corresponding female rail of the optical assembly unit.

6. The portable interferometric system of claim 1, wherein the sensing layer comprises one or more antigens, antibodies, DNA, aptamers, polypeptides, nucleic acids, carbohydrates, lipids, or molecularly imprinted polymers, or immunoglobulins suitable for binding one or more analytes within an aquatic test sample composition.

7. The portable interferometric system of claim 1, wherein the system is configured to analyze the light signals from two or more waveguide channels to detect the presence of an analyte that individual waveguide channels could not have detected alone.

8. The portable interferometric system of claim 1, wherein the one or more waveguide channels each comprises a different sensitive layer to allow the system to detect different analytes on each waveguide channel.

9. The portable interferometric system of claim 1, wherein the sensitive layer is configured to bind one or more antibodies, virus antigens, virus proteins, bacteria, fungi, pathogen, RNA, chemical, mRNA or any combination thereof.

10. The portable interferometric system of claim 1, having an analyte detection limit down to about 1.0 picogram/L.

11. The portable interferometric system of claim 1, having an analyte detection limit down to about 1000 pfu/ml.

12. The portable interferometric system of claim 1, wherein the detector has sensitivity to at least 2 pixels per diffraction line pair.

13. The portable interferometric system of claim 1, further comprising a location means adapted to determine the physical location of the system.

14. The portable interferometric system of claim 1, wherein the analyte is one or more of a fungicide, herbicide, plant growth regulator, insecticide, fungus, bacterium, or microbe.

15. A method of detecting and quantifying the level of analyte in an aquatic test sample composition, the method comprising the steps of:
- collecting an aquatic target sample containing one or more analytes;
- optionally entering an identification associated with the target sample;
- introducing the aquatic target sample to a system of claim 1;
- optionally, mixing the target sample with a buffer solution to form an aquatic test sample composition;
- initiating waveguide interferometry on the test sample composition;
- processing any data resulting from the waveguide interferometry; and
- optionally, transmitting any data resulting from the waveguide interferometry.

16. The method of claim 15, wherein the step of transmitting data includes wirelessly transmitting analyte detection and quantification data to a mobile device or server.

17. The method of claim 15, further comprising the step of displaying data related to the presence of analyte in the test sample composition on the display unit.

18. The method of claim 15, wherein the aquatic target sample is collected from salt water, fresh water, fish farm, effluent system, waterway, water reservoir, potable water source, or sanitary sewer.

19. The method of claim 18, wherein the aquatic target sample is in the form of, dissolved in, or suspended in a liquid or a gas.

20. The method of claim 15, wherein the data resulting from the waveguide interferometry is provided at or under 30 minutes.

21. The portable interferometric system of claim 1, wherein the cartridge housing comprises a vent port for allowing air to exit and prevent bubble formation.

* * * * *